United States Patent
Hardeman et al.

(10) Patent No.: US 10,426,254 B2
(45) Date of Patent: Oct. 1, 2019

(54) SYSTEMS AND METHODS FOR PROVIDING ANGLE GUIDANCE FOR A USER OPERATING AN ORAL HYGIENE DEVICE

(71) Applicant: KONINKLIJKE PHILIPS N.V., Eindhoven (NL)

(72) Inventors: Toon Hardeman, s-Hertogenbosch (NL); Vincent Jeanne, Bothell, WA (US); Hubert Jean Joseph Amaury Vroomen, Venray (NL); Arjen Den Hamer, Helmond (NL); Martin John Edwards, Solihull (GB); Jan Wojciech Obrebski, Waalre (NL); Alex Merck, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 100 days.

(21) Appl. No.: 15/569,631

(22) PCT Filed: Apr. 29, 2016

(86) PCT No.: PCT/IB2016/052431
§ 371 (c)(1),
(2) Date: Oct. 26, 2017

(87) PCT Pub. No.: WO2016/174621
PCT Pub. Date: Nov. 3, 2016

(65) Prior Publication Data
US 2018/0352947 A1 Dec. 13, 2018

Related U.S. Application Data

(60) Provisional application No. 62/154,327, filed on Apr. 29, 2015.

(51) Int. Cl.
| | |
|---|---|
| A61C 17/22 | (2006.01) |
| A61C 17/34 | (2006.01) |
| A46B 15/00 | (2006.01) |
| A46B 9/04 | (2006.01) |

(Continued)

(52) U.S. Cl.
CPC ........ *A46B 15/0012* (2013.01); *A46B 5/0095* (2013.01); *A46B 9/04* (2013.01);
(Continued)

(58) Field of Classification Search
CPC ........... A61C 17/22; A61C 17/34; A46B 9/04; A46B 5/0095
See application file for complete search history.

(56) References Cited

U.S. PATENT DOCUMENTS

| | | |
|---|---|---|
| 8,159,352 B2 | 4/2012 | Jimenez et al. |
| 8,176,591 B2 | 5/2012 | Iwahori et al. |

(Continued)

FOREIGN PATENT DOCUMENTS

| | | |
|---|---|---|
| CN | 102018363 A | 4/2011 |
| DE | 102013101908 A1 | 8/2014 |

(Continued)

*Primary Examiner* — Michael D Jennings

(57) ABSTRACT

An oral hygiene device (100) including at least one sensor (104) to improve a user's operation of the oral hygiene device is provided. In one exemplary embodiment, the oral hygiene device includes a longitudinal shaft (102), an attachment assembly (112), a handle portion (110), a suspension system (106), at least two sensors (104a, 104b), and at least one processor (132). The at least one processor is operable to receive an amount of force applied to the attachment assembly, which is detected by the at least two sensors. An angle that the attachment assembly is applied is also determined, the angle being based on the detected amount of force. In one embodiment, the angle and the amount of force are displayed within a user interface to the user to help the user improve their oral hygiene technique.

13 Claims, 16 Drawing Sheets

(51) Int. Cl.
*A46B 5/00* (2006.01)
*G09B 5/02* (2006.01)
*G09B 19/00* (2006.01)

(52) U.S. Cl.
CPC ...... *A46B 15/0006* (2013.01); *A46B 15/0038* (2013.01); *A61C 17/22* (2013.01); *A61C 17/221* (2013.01); *A61C 17/34* (2013.01); *G09B 5/02* (2013.01); *G09B 19/0084* (2013.01); *A46B 2200/1066* (2013.01)

(56) References Cited

U.S. PATENT DOCUMENTS

| | | | |
|---|---|---|---|
| 8,341,791 B2 | 1/2013 | Iwahori | |
| 8,393,037 B2 | 3/2013 | Iwahori et al. | |
| 8,585,411 B2 | 11/2013 | Puurunen | |
| 10,064,711 B1 * | 9/2018 | Richter | A61C 17/221 |
| 2009/0092955 A1 * | 4/2009 | Hwang | A46B 15/0002 |
| | | | 434/263 |
| 2011/0010875 A1 * | 1/2011 | Iwahori | A46B 15/0006 |
| | | | 15/22.1 |
| 2011/0247156 A1 | 10/2011 | Schmid et al. | |
| 2012/0198640 A1 * | 8/2012 | Jungnickel | A46B 15/0012 |
| | | | 15/105 |
| 2012/0310593 A1 | 12/2012 | Bates et al. | |

FOREIGN PATENT DOCUMENTS

| | | |
|---|---|---|
| WO | 2010151582 A1 | 12/2010 |
| WO | 2012020165 A1 | 2/2012 |
| WO | 2016055925 A1 | 4/2016 |

* cited by examiner

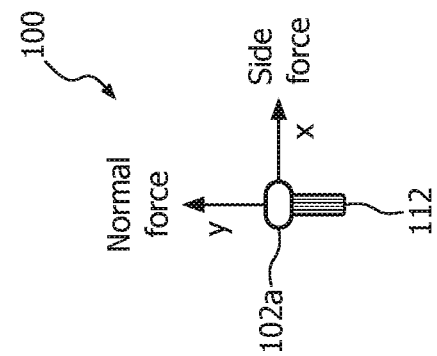
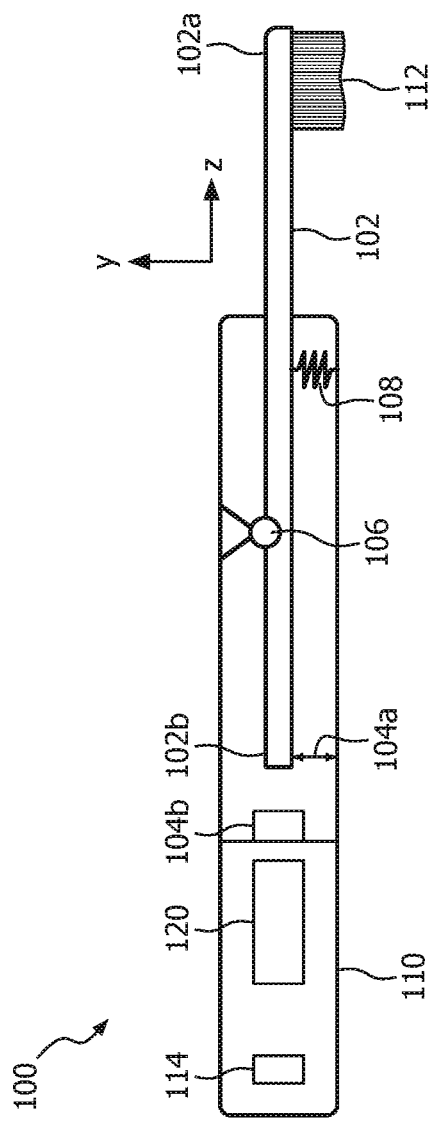
FIG. 1A
FIG. 1B

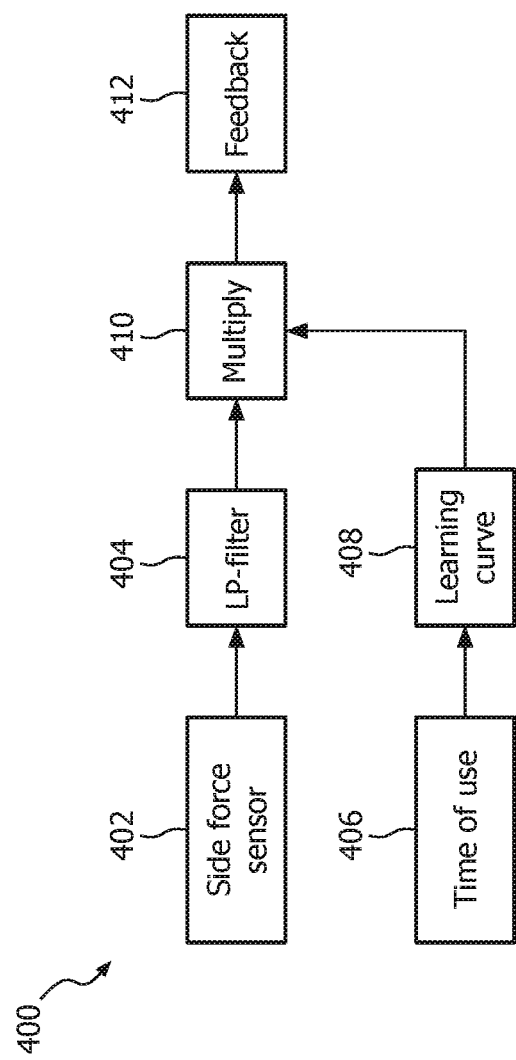

SYSTEMS AND METHODS FOR PROVIDING ANGLE GUIDANCE FOR A USER OPERATING AN ORAL HYGIENE DEVICE

CROSS-REFERENCE TO PRIOR APPLICATIONS

This application is the U.S. National Phase application under 35 U.S.C. § 371 of International Application No. PCT/IB2016/052431, filed on Apr. 29, 2016 which claims the benefit of U.S. Provisional Patent Application No. 62/154,327, filed on Apr. 29, 2015. These applications are hereby incorporated by reference herein.

BACKGROUND OF THE INVENTION

1. Field of the Invention

The present invention generally relates to oral hygiene devices and, in particular, oral hygiene devices including at least one sensor capable of determining an amount of side force applied by a user operating the oral hygiene device, which is related to a brushing angle. Additionally, the present invention also generally relates to a user device capable of receiving data from an oral hygiene device, and displaying information, based on the received data, within a user interface to guide a user operating the oral hygiene device to improve their oral hygiene technique.

2. Description of the Related Art

Oral hygiene devices, such as electric toothbrushes or power toothbrushes, typically rely on a set of bristles moved by a driving mechanism to brush a surface of a user's teeth, gums, and/or tongue. It has been established that to produce optimal effects, the bristles should be applied substantially perpendicular to the user's teeth, gums, and/or tongue when in use. However, in common, everyday practice, individuals tend to not apply a correct brushing angle. This may be due, amongst other factors, to improper technique of the user, and/or varying surface angles and surface types within the user's mouth. For example, a user's front teeth may be oriented at a different angle than a user's back teeth. Furthermore, individuals tend to apply either too much or too little pressure when brushing their teeth and as such, ineffective brushing due to incorrect brushing angles is further exacerbated.

A brushing angle is typically defined relative to an individual's, for example, the angle between a surface of an individual's teeth and a brush head of a toothbrush. For a correct brushing angle, any variation in a geometry of an individual's mouth, and/or any motion of the oral hygiene device (e.g., toothbrush) by the user, should be compensated by the user operating the oral hygiene devices. This may require a direct measurement between the user's teeth and the brush head as opposed to a more common measurement of the brush head relative to a fixed coordinate system Correcting the issues mentioned above is not intuitive. Most oral hygiene devices do not provide individuals with the capability of quickly seeing the errors in their brushing technique and altering their brushing technique accordingly. Thus, it would be beneficial for there to be improved systems and methods capable of determining an amount of pressure being applied while brushing one's teeth, gums, and/or tongue, as well as an angle of the applied pressure when brushing (e.g., the brushing angle). Furthermore, it would be beneficial for there to be systems and methods that provide individuals with an intuitive means to view any deficiencies in their brushing technique, and how the deficiencies may be corrected in real-time.

SUMMARY OF THE INVENTION

Accordingly, it is an objective of this invention to provide an oral hygiene device, such as an electronic toothbrush, that is capable of determining an amount of side force applied by the oral hygiene device when operated by a user. This objective is achieved according to the present invention by acquiring data from one or more sensors within the oral hygiene device to determine an angle that an attachment assembly of the oral hygiene device is being applied at, as well as to determine an amount of force being applied to the attachment assembly. Furthermore, another objective of this invention is to provide feedback to the user operating the oral hygiene device regarding the quality of their operation of the oral hygiene device. This objective is achieved according to the present invention by presenting the determined angle and force of the attachment assembly to the user such that the user is capable of viewing when the angle and force of the attachment assembly are within correct ranges for proper oral hygiene care and if not in which direction to improve.

In a first exemplary embodiment, an oral hygiene device is provided. The oral hygiene device of the first exemplary embodiment includes a longitudinal shaft, an attachment assembly located at a first end of the longitudinal shaft, and a handle portion. The handle portion includes a portion of the longitudinal shaft including a second end of the longitudinal shaft, and at least one sensor operable to detect an amount of side force applied to the attachment assembly. The oral hygiene device also includes at least one processor operable to determine an angle that the attachment assembly is applied at based on the detected amount of side force.

In a second exemplary embodiment, a method for providing feedback to a user operating an oral hygiene device regarding an angle of application of the oral hygiene device is provided. In one embodiment, first data from a side force sensor located within a handle portion of the oral hygiene device is received. The first data corresponds to an amount of side force applied to an attachment assembly of the oral hygiene device. Second data is obtained from at least one acceleration sensor of the oral hygiene device, the second data corresponding to an amount of gravitational force associated with the oral hygiene device. A position of the attachment assembly within a mouth of a user operating the oral hygiene device is also estimated. The first data, second data, and the estimated position are combined to determine at least one of an overall angle and amount of overall force of the attachment assembly as it is being applied. Feedback is then provided to the user operating the oral hygiene device, where the feedback includes at least one of the overall angle and the overall amount of force of the applied attachment assembly.

In a third exemplary embodiment, a user device for providing feedback to a user operating an oral hygiene device is provided. The user device includes a display screen, communications circuitry, and at least one processor. The at least one processor, in one embodiment, is operable to receive data from at least one sensor located on the oral hygiene device via the communications circuitry. The data corresponds to an amount of side force applied to an attachment assembly of the oral hygiene device, an amount of gravitational force exerted on the attachment assembly of the oral hygiene device, and a position estimate of the attachment assembly within the user's mouth. The at least one processor is further operable to determine, based on the received data, an angle that the attachment assembly of the oral hygiene device is being applied at, and an amount of force applied by the user to the attachment assembly while interacting with the user's mouth. Furthermore, the at least one processor is operable to display feedback on the display screen of the user device. The feedback, in one embodiment, includes information regarding a quality of the angle and the amount of force of the attachment assembly based on a predefined angle for the attachment assembly to be applied and a predefined amount of force to be applied by the attachment assembly.

BRIEF DESCRIPTION OF THE DRAWINGS

The above and other features of the present invention, its nature and various advantages will be more apparent upon consideration of the following detailed description, taken in conjunction with the accompanying drawings in which:

FIGS. 1A and 1B are illustrative diagrams of a side view and a front view, respectively, of an oral hygiene device 100 in accordance with various embodiments;

FIG. 7 is an illustrative flowchart of a process 400 in accordance with various embodiments;

DETAILED DESCRIPTION OF EXEMPLARY EMBODIMENTS

Figure 2:
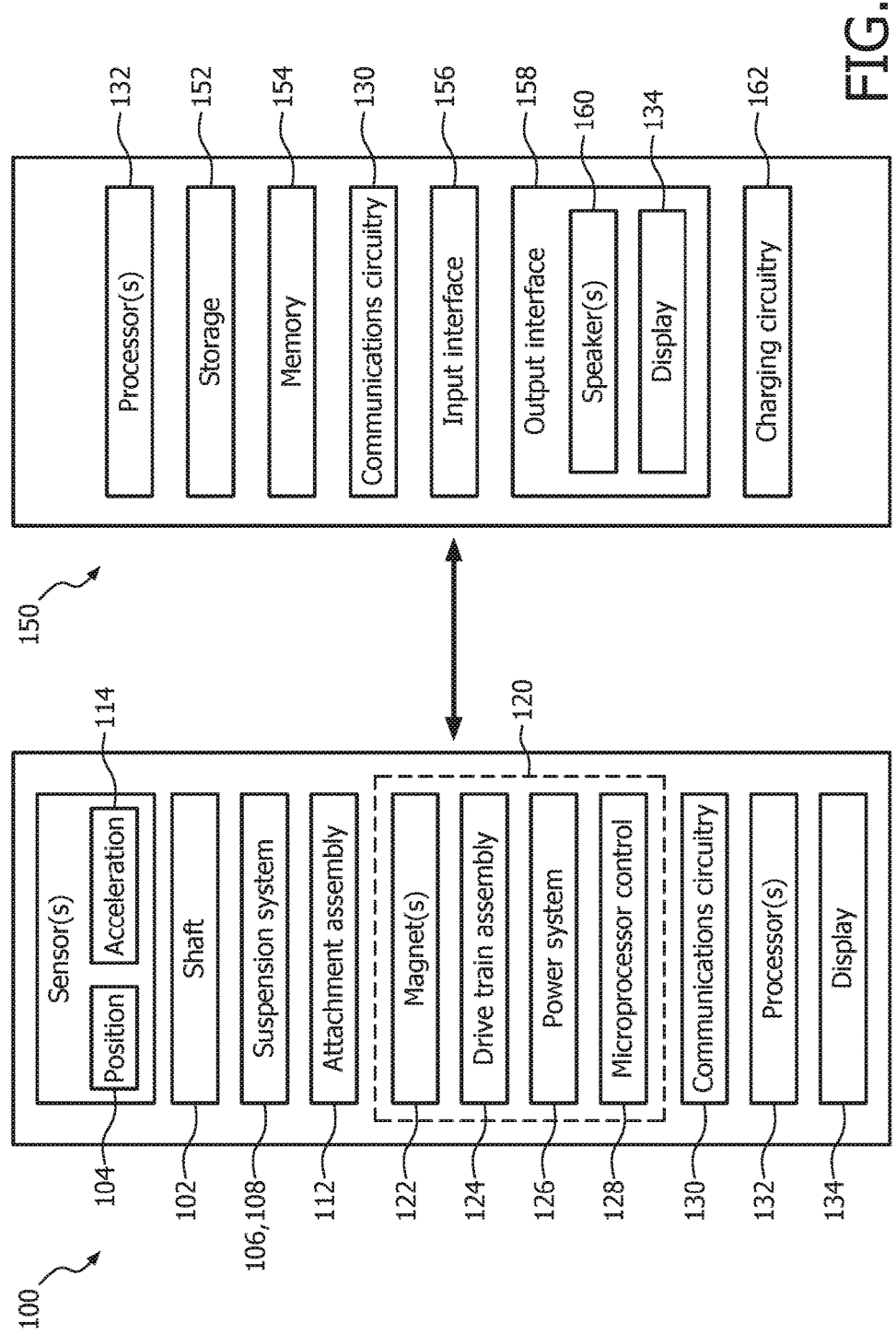
FIG. 2 is an illustrative block diagram of oral hygiene device 100 and a user device 150 in accordance with various embodiments.

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise.

As used herein, the word "number" shall mean one or an integer greater than one (e.g., a plurality). As used herein, "perpendicular" or "substantially perpendicular" shall mean at an angle of 90 degrees±5 degrees. As used herein, "parallel" or "substantially parallel" shall mean at an angle of 0 degrees±5 degrees. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIGS. 1A and 1B are illustrative diagrams of a side view and a front view, respectively, of oral hygiene device 100 in accordance with various embodiments. Oral hygiene device 100, in the illustrative non-limiting embodiment, includes an attachment assembly 112 located at a first end 102a of a longitudinal shaft 102. Attachment assembly 112 may be a component coupled or fixed to first end 102a of longitudinal shaft 102. For example, attachment assembly 112 may be removable from first end 102a of longitudinal shaft and switched with a different type of attachment assembly 112. As another example, attachment assembly 112 may be manufactured with longitudinal shaft 102 such that the two form a single structure. Various types of attachment assemblies 112 include, but are not limited to, brush head assemblies including a plurality of bristles attached to a bristle member, a floss head, a water cleaning mechanism, or any other type of oral hygiene interface, or any combination thereof.

A handle portion 110 includes a portion of longitudinal shaft 102 including a second end 102b of longitudinal shaft 102. Handle portion 110, in one embodiment, is substantially annular about a longitudinal axis (e.g., a z-axis) defined by longitudinal shaft 102. Housed within handle portion 110 is a suspension system 106 including a stiffener 108. Suspension system 106 allows longitudinal shaft 102 to move freely during normal operating conditions. For example, longitudinal shaft 102 may rotate about the z-axis in a rotational manner. Stiffener 108, in one embodiment, is any elastic spring element that has a predefined stiffness for sideward movement (e.g., translational movement about an x-axis) or a direction of a side force applied to attachment assembly 112, and/or rotational movement about a radial axis of handle portion 110 (e.g., a y-axis) or a direction of a normal force applied to attachment assembly 112. For example, stiffener 108 may be any substantially flat resilient biasing member, such as a leaf spring.

In one embodiment, handle portion 110 also includes one or more sensors mounted therein, such as first and second position sensors 104a and 104b. In one embodiment, position sensor 104a is operable to measure an amount of movement of longitudinal shaft 102 along the y-axis or an amount of normal force applied to attachment assembly 112, whereas position sensor 104b is operable to measure an amount of translational movement of longitudinal shaft 102 in the x-direction, or an amount of side force applied to attachment assembly 112. Persons of ordinary skill in the art will recognize that although oral hygiene device 100 includes two positions sensors 104a and 104b operable to measure movement of longitudinal shaft 102 along two separate axes, any number of sensors may be used to measure any number of directional movements of longitudinal shaft 102, and the aforementioned is merely exemplary. For example, only one position sensor 104a, 104b may be included within handle portion 110 of oral hygiene device 100, which may be operable to measure multiple direction movements (e.g., along the x- and y-axis). As another example, three position sensors may be included within handle portion 110 of oral hygiene device 100, which may be operable to each measure one direction (e.g., along the x-, y-, z-axis). In one embodiment, one or more of sensors 104a and 104b in combination with stiffener 108 may form a force sensor capable of measuring an amount of force applied to attachment assembly 112 in one or more directions.

In one embodiment, sensors 104a and/or 104b are Hall Effect sensors capable of measuring a strength of a magnetic field within handle portion 110 at a respective position. A magnetic field is capable of being generated by a magnetic assembly 120, which may include one or more magnetics capable of producing a magnetic field, which is described in greater detail below. Application of Hall Effect sensors 104a and 104b, in the exemplary embodiment, to measure the magnetic field strength and the stiffness of stiffener 108 create a built-in force sensor for oral hygiene device 100. Persons of ordinary skill in the art will recognize that sensors 104a and 104b may be any type of sensor including, but not limited to, capacitive sensors, induction sensors, piezo restrictive sensor, and/or optical sensors. Furthermore, in one embodiment, one or more additional sensors are included within oral hygiene device 100. For example, attachment assembly 112 may include one or more sensors in addition to, or instead of, sensors 104a, 104b located within handle portion 110.

Oral hygiene device 100 further includes, in the illustrated embodiment, an acceleration sensor(s) 114. Acceleration sensor 114 is operable to measure an amount force applied to oral hygiene device 100 due to gravity (e.g., gravitational force). For example, acceleration sensor(s) 114 may be capable of detecting an angle of handle 110 of oral hygiene device 100 with respect to a direction of gravity, a motion of oral hygiene device 100 with respect to gravity, and/or a position of oral hygiene device 100. In one embodiment, acceleration sensor(s) 114 may include multiple accelerometers located at various points through oral hygiene device such that measurements with respect to gravity may be obtained for various portions of oral hygiene device. For example, one accelerometer may be located at first end 102a of longitudinal shaft 102 and a second accelerometer may be located at an end portion of handle portion 110 proximate second end 102b of longitudinal shaft 102.

FIG. 2 is an illustrative block diagram of oral hygiene device 100 and user device 150 in accordance with various embodiments. Magnetic assembly 120 of oral hygiene device 100 further includes a drive train assembly 124 that is resonantly driven by a power system 126 which includes a battery and an electronics carrier (e.g., a printed circuit board of PCB). A rubber bumper also may be included within oral hygiene device 100 which cushions drive train assembly 124 within handle portion 110. Oral hygiene device 100 further includes a printed circuit board with a microprocessor control 128 for creating a drive signal for power system 126. At a rear end of drive train assembly 126 is one or more magnet(s) 122, which, in one embodiment, is positioned adjacent to sensors 104a, 104b.

Oral hygiene device 100 further includes, in one exemplary embodiment, communications circuitry 130, one or more processors 132, and a display 134. Processor(s) 132 may include any processor circuitry, such as one or more processors capable of controlling the operations and functionality of oral hygiene device 100. In one embodiment, processor(s) 132 facilitates communications between various components within oral hygiene device 100 (e.g., sensor(s) 104a, 104b and/or accelerometer 114 and communications circuitry 130).

Communications circuitry 130, in one embodiment, includes any circuitry capable of connecting to a communications network and/or transmitting communications (e.g., voice and/or data) to one or more user devices and/or servers. Communications circuitry 130 is also capable of interfacing with one or more communications networks using any suitable communications protocol including, but not limited to, Wi-Fi (e.g., 802.11 protocol), Bluetooth®, radio frequency systems (e.g., 900 MHz, 1.4 GHz, and 5.6 GHz communications systems), infrared, GSM, GSM plus EDGE, CDMA, quadband, VOIP, or any other protocol, or any combination thereof.

Display 134, in one embodiment, corresponds to any type of display capable of presenting content to a user and/or on oral hygiene device 100. Display 134 is operable to be any size or shape, and may be located on one or more regions of oral hygiene device 100. Various display types include, but are not limited to, liquid crystal displays ("LCD"), monochrome displays, color graphics adapter ("CGA") displays, enhanced graphics adapter ("EGA") displays, variable graphics array ("VGA") displays, or any other display type, or any combination thereof. In one embodiment, display 134 is a touch screen and/or an interactive display. In another embodiment, display 134 is a touch screen including a multi-touch panel coupled to processor(s) 132 of oral hygiene device 100. In still another embodiment, display 134 is a touch screen including capacitive sensing panels. Persons of ordinary skill in the art will recognize that the characteristics of display 134 may depend on the size, shape, and/or production costs of oral hygiene device 100. For example, if oral hygiene device 100 is small, then the amount of space is limited and display 134 may only include a black and white interface operable to display alphanumeric characters.

One or more of the aforementioned components of oral hygiene device 100 may be combined or omitted without deviating from the scope of the present invention. For example, oral hygiene device 100 may not include communications circuitry 130 and/or display 134. As another example, oral hygiene device 100 may include one or more storage mediums, speakers, and/or input components.

User device 150 of FIG. 2 is any suitable user device operable to interact with oral hygiene device 100. For example, user device 150 may correspond to a smart phone or tablet computers that receives data from sensors 104a, 104b and generates feedback that may be presented to a user on user device 150. As another example, user device 150 may correspond to a base station for oral hygiene device 100, serving to provide electrical charge to a battery within oral hygiene device 100, a place to store or rest oral hygiene device 100 when not in use, and/or feedback to a user operating oral hygiene device 100.

User device 150, in the illustrative exemplary embodiment, includes one or more processors 132, storage 152, memory 154, communications circuitry 130, an input interface 156, an output interface 160, and charging circuitry 162. Output interface 160 further includes one or more speakers 160 and display 134. In one embodiment, processor(s) 132, communications circuitry 130, and display 134 are substantially similar to the aforementioned descriptions corresponding to oral hygiene device 100, with the exception that the former reside on user device 150 and therefore may include one or more additional features. For example, an amount of real estate available on user device 150 may be larger than that of oral hygiene device 100, and therefore display 134 on user device 150 may be larger and/or more robust (e.g., a touch-sensitive display screen). As another example, processor(s) 132 of user device 150 may be more powerful than processor(s) 132 of oral hygiene device 100.

Storage 152, in one embodiment, includes one or more storage mediums. Various types of storage mediums include, but are not limit to, hard-drives, solid state drives, flash memory, permanent memory (e.g., ROM), or any other storage type, or any combination thereof. Any form of data or content may be stored within storage 152, such as photographs, music files, videos, applications, documents, data spreadsheets, or any other data file, or any combination thereof.

Memory 154, in one embodiment, includes cache memory, semi-permanent memory (e.g., RAM), or any other memory type, or any combination thereof. In one embodiments, memory 154 may be used in place of and/or in addition to external storage for storing data on oral hygiene device 100. However, persons of ordinary skill in the art will recognize that storage 152 and memory 154 may be combined into a single component.

Input interface 156, in one embodiment, includes any suitable mechanism or component for receiving inputs from a user operating user device 150. For example, input interface 156 may include a camera capable of capturing images and/or photos. Furthermore, in addition to or instead of a camera, input interface may include one or more of a keyboard, mouse, joystick, or a touch-sensitive interface (e.g., a touch-sensitive display screen).

Output interface, in one embodiment, includes one or more speakers 160 and display 134. Speaker 160, in one embodiment, corresponds to any suitable mechanism for outputting audio signals. For example, speaker 160 may include one or more speaker units, transducers, or array of speakers and/or transducers capable of broadcasting audio signals and audio content to a user interfacing with user device 150. In one embodiment, speaker 160 corresponds to headphones or ear buds capable of broadcasting audio directly to a user operating user device 150.

In one embodiment, user device 150 includes charging circuitry 162 that is capable of charging a battery on oral hygiene device 100. For example, user device 150 may be a base station compatible with oral hygiene device 100. Charging may be performed via a direct electrical coupling between user device 150 and oral hygiene device 100 or passively using inductive charging techniques. In one embodiment, user device 150 is coupled to an external power source, such as a power outlet, which provides electrical charge to charging circuitry 162 of user device 150, which is then transferred to a battery within oral hygiene device 100.

Figure 3B:
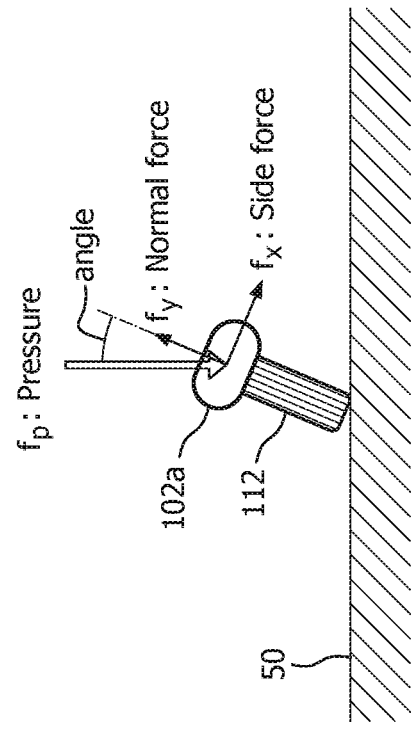
FIGS. 3A and 3B are illustrative diagrams of an implementation of oral hygiene device 100 in accordance with various embodiments.
Figure 3A:
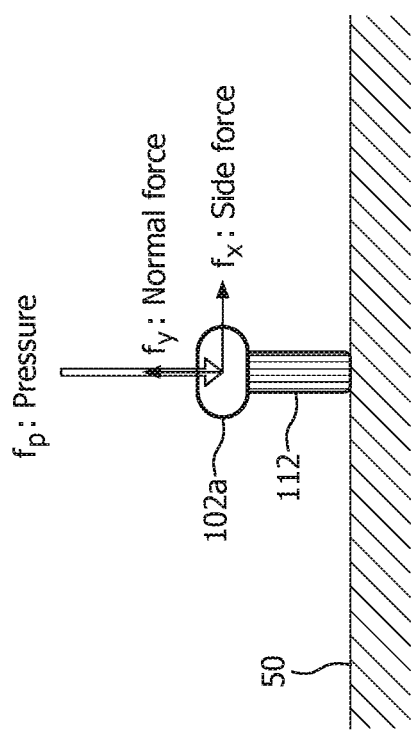

FIGS. 3A and 3B are illustrative diagrams of an implementation of oral hygiene device 100 in accordance with various embodiments. In one exemplary embodiment, oral hygiene device 100 interacts with a surface 50 of a user's mouth (e.g., teeth, tongue, gums, etc.). As seen in FIG. 3A, attachment assembly 112 of oral hygiene device 100 is applied to surface 50 such that the applied force or pressure, $f_p$, is substantially perpendicular to surface 50. When $f_p$ is substantially perpendicular to surface 50, side force $f_x$ is approximately zero and the normal force $f_y$ equals the applied force $f_p$ in an opposite direction but with approximately equal magnitude. If attachment assembly 112 includes bristles such that a brushing motion occurs on ones teeth via application of applied force $f_p$, then maximum brushing effectiveness will occur because there is essentially no side force component and all brushing force resides perpendicular to the brushing surface 50.

If the applied force $f_p$ is not perpendicular to surface 50, as seen in FIG. 3B, there is a non-zero side force $f_x$ component, and the normal force $f_y$ decreases by a factor of $f_p \cos \alpha$, where $\alpha$ is the angle of that attachment assembly 112 is applied to surface 50. In this particular scenario, the efficacy of a user's brushing decreases. This is because the side force component $f_x$ is non-zero, and the amount of force applied to the brushing surface 50 along the y-axis less than the maximum amount. This is less than the ideal brushing technique, as proper brushing technique corresponds to essentially zero side force, thereby providing the best oral hygiene results. For example, an ideal brushing technique may have the bristles of the oral hygiene device contact the gum line and just between the gum and the teeth.

Figure 4:
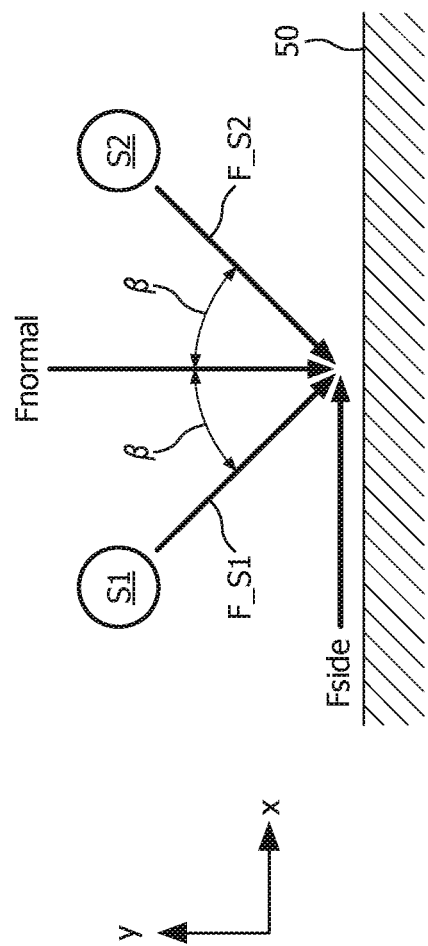
FIG. 4 is another illustrative diagram of a multi-sensor implementation of oral hygiene device 100 in accordance with various embodiment.

FIG. 4 is another illustrative diagram of a multi-sensor implementation of oral hygiene device 100 in accordance with various embodiment. In the exemplary embodiment, a first sensor S1 measures a force along one direction and a second sensor S2 measures a force along a second direction. Each sensor is capable of decomposing the measured forces into a side force component and a normal force component. For example, first sensor S1 measures a force $F_{S1}$ that has an angle of incidence of $\beta$ with respect to the normal of surface 50. The amount of side force from $F_{S1}$ is then equal to $F_{S1} \sin \beta$, whereas the amount of in the direction of the normal force equals $F_{S1} \cos \beta$. Similar component breakdowns of a force $F_{S2}$ are calculable. It should be understood that the normal force is typically referred to as an amount of force opposing an incident force by a surface, and thus although the normal force has been described as approaching surface 50, this is merely exemplary, and the actual normal force may equal $-F_{Normal}$.

The relationship of force $F_{S1}$ and $F_{S2}$ to side force $F_{side}$ and normal force $F_{normal}$ are thus determined using the following relationships:

$$F_{side} = \sin(\beta)F_{S1} - \sin(\beta)F_{S2};$$

$$F_{normal} = \cos(\beta)F_{S1} + \cos(\beta)F_{S2}$$

Where $F_{side}$ equals the difference between the side-component (e.g., along the x-axis) of $F_{S1}$ and $F_{S2}$, and $F_{normal}$ equals the aggregate of the normal-component (e.g., along the y-axis) of $F_{S1}$ and $F_{S2}$. The sensors detecting forces $F_{S1}$ and $F_{S2}$ are scalars in general, however as they detect force amounts in certain directions, it is possible to view them as vectors. Regardless, persons of ordinary skill in the art will recognize that any combination of sensors may be sued to extract relative force values for particular directions, and the aforementioned are merely exemplary.

Figure 5A:
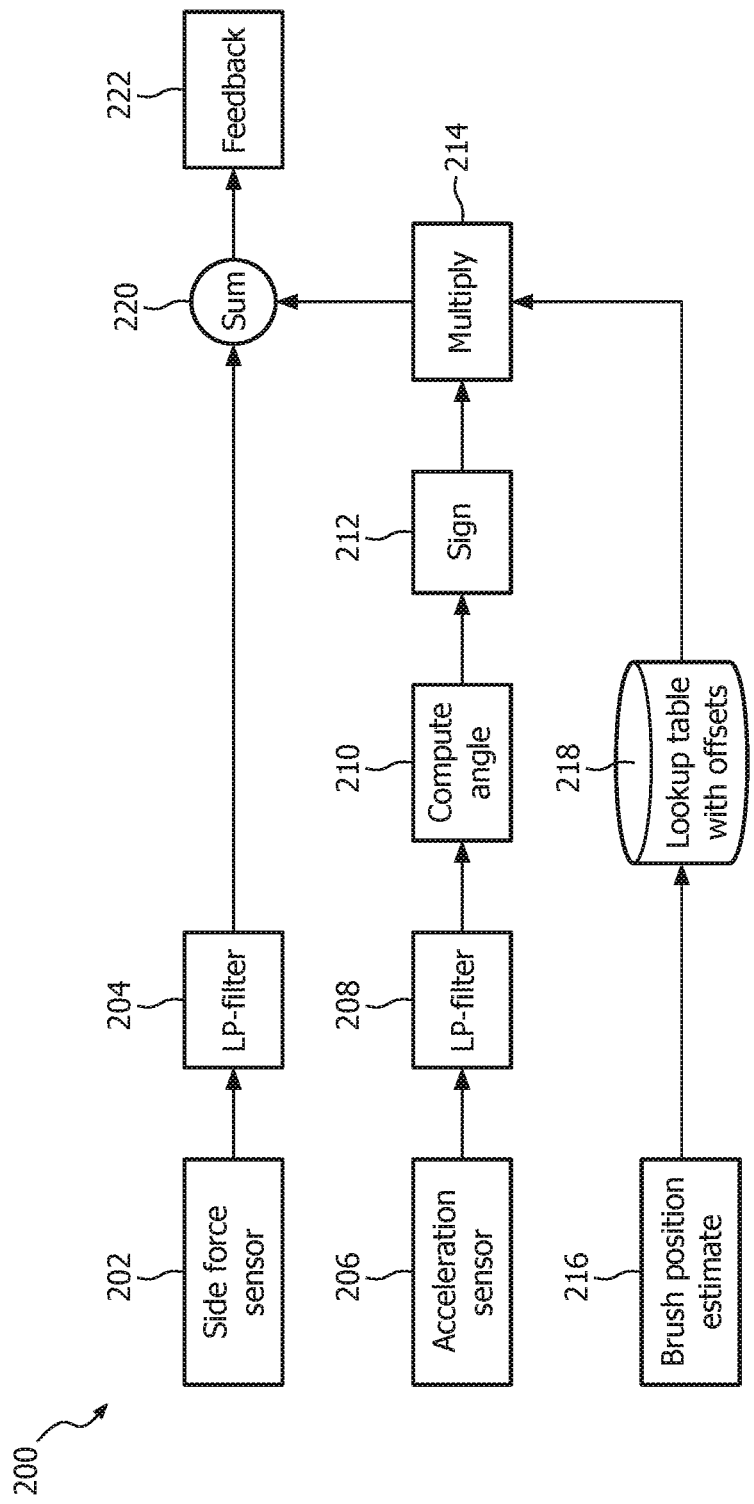
FIG. 5A is an illustrative flowchart of a process 200 in accordance with various embodiments.

FIG. 5A is an illustrative flowchart of process 200 in accordance with various embodiments. Process 200 begins at step 202 with a measurement being obtained from one or more side force sensors 104a, 104b of oral hygiene device 100. For example, an amount of side force $F_{side}$, as seen in FIG. 4, is obtained from sensors within oral hygiene device 100 to determine how much force a user may be applying to their teeth/gums in a direction orthogonal to the normal force.

At step 204, a low pass filter is applied to the measurements obtained at step 202. Application of the low pass filter, in one embodiment, removes erroneous or irrelevant signals obtained by side force sensors 104a, 104b. For example, the low pass filter may have a cut-off frequency of a few Hertz, such as 4 Hz. Any signal detected by sensors 104a, 104b having a frequency greater than 4 Hz, in this example, would therefore be removed. One exemplary type of low pass filter that may be used is a low order Butterworth filter.

In one embodiment, after the low pass filter is applied at step 204, process 200 proceeds to step 222 where feedback is provided to the user operating oral hygiene device 100. The feedback is based on only the filtered measurements from the low pass filter in this particular embodiment, and therefore, may serve as a rough approximation of the angle that attachment assembly 112 of oral hygiene device 100 is being applied to surface 50. However, greater precision is possible in certain scenarios.

In one embodiment, a position within a user's mouth where oral hygiene device 100 is being applied will affect the measurements of side force sensors 104a, 104b. For example, if the user is operating oral hygiene device 100 in the front of their mouth, the angle of attachment assembly 112 of oral hygiene device 100 with respect to the surface of the user's teeth in the front of their mouth should be substantially perpendicular. However, if the user is operating oral hygiene device 100 in the back of their mouth, such as brushing the back molar teeth, the angle that attachment assembly 112 of oral hygiene device 100 with respect to the user's teeth may differ. This is due to the fact that the gums in the back of the user's mouth, or at other various positions within the user's mouth, is thicker resulting in a slightly different angle with respect to the teeth in the front of the user's mouth. The sign (e.g., plus/minus) of the required correction of the measured side force depends on the orientation of handle portion 110 with respect to the user's mouth. This orientation, in one embodiment, is measured using acceleration sensor(s) 114.

Figure 5C:
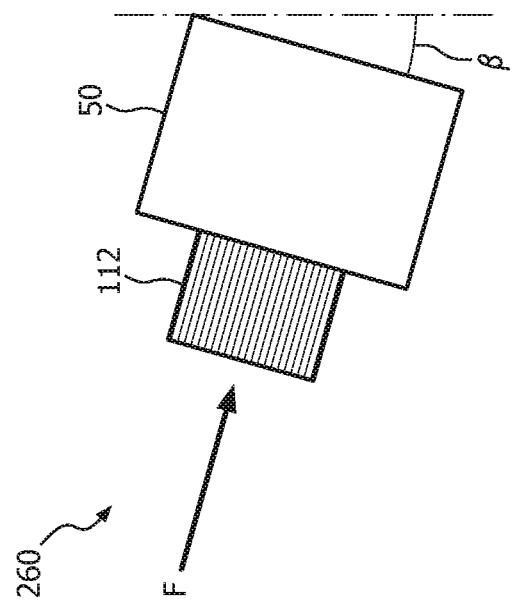
FIGS. 5B and 5C are illustrative diagrams of various angles of oral hygiene device 100 based on a position of oral hygiene device 100 within the user's mouth in accordance with various embodiments.
Figure 5B:
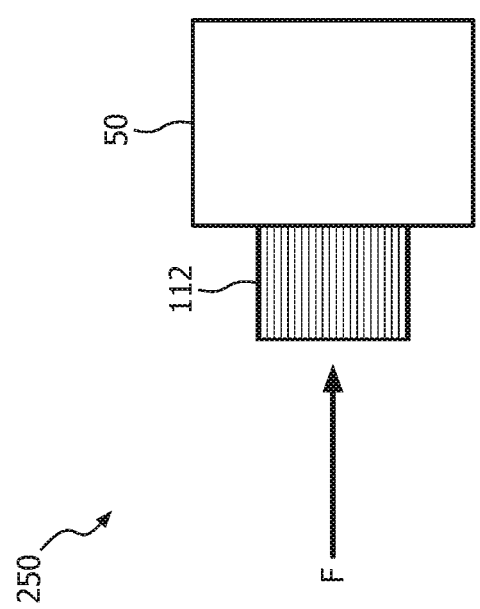

FIGS. 5B and 5C are illustrative diagrams of various angles of oral hygiene device 100 based on a position of oral hygiene device 100 within the user's mouth in accordance with various embodiments. As seen in a first scenario 250, attachment assembly 112 of oral hygiene device 100 is applied to surface 50 with a force F at a substantially perpendicular angle. In other words, the amount of side force applied to surface 50 by attachment assembly 112 of oral hygiene device 100 is substantially zero. As seen in a second scenario 260, attachment assembly 112 also applies force F to surface 50 at a substantially perpendicular angle such that the amount of side force is substantially zero, however, force F is at slightly different angle than in first scenario 250. In second scenario 260, surface 50 is orientated at an angle Φ with respect to a vertical axis, and therefore force F is also applied at angle Φ with respect to the horizontal of first scenario 250. This exemplary embodiment corresponds to two different scenarios where a user's teeth may be orientated at different angles.

Returning to process 200 of FIG. 5A, at step 216, a position estimate of attachment assembly 112 is capable of being made to determine an approximate position of attachment assembly 112 within the user's mouth. In one embodiment, oral hygiene device 100 is capable of recognizing a position within the user's mouth of attachment assembly 112, and based on the position, determine an angle offset, at step 218, for oral hygiene device 100. For example, a light sensor, proximity sensor, and/or any other type of sensor may be used to determine a relative position of attachment assembly 112 within the user's mouth, however persons of ordinary skill in the art will recognize that the aforementioned are merely exemplary. A lookup table may be used to determine, based on the position within the user's mouth of attachment assembly 112, an angle offset based on the orientation of one or more teeth at that position. The lookup table may inventory multiple positions within a user's mouth and store an offset associated with each position. These offsets may correspond to an orientation of a user's teeth or gums at that particular position, and may be used to offset the detected amount of side force. The offset may also depend on the applied normal force. In this particular scenario, the offsets stored in the look up table may be equal to the tangent of the angle between the side force and the normal force.

In one embodiment, estimation of the position of attachment assembly 112 of oral hygiene device 100 is performed by one or more of a light sensor, a voice sensor, or any other type of sensor, or any combination thereof. For example, a light sensor may be used to determine how bright the area surrounding attachment assembly 112 is, and based on the determined brightness, an estimation of where attachment assembly 112 is within the user's mouth may be performed. A user's front teeth may, for example, be a more brightly lit region than a user's back teeth. As another example, a voice sensor may be used to determine a position of attachment assembly 112 of oral hygiene device 100 by listening for specific sounds or tones. For instance, a user's front teeth may produce a specific sound when brushed which may differ from a user's back teeth. As another example, a user may vocally produce tones which may inform oral hygiene device 100 an approximate position of attachment assembly 112. As yet another example, the user can also be provided instructions from oral hygiene device 100 to move oral hygiene device 100 towards a certain position within the user's mouth.

In one embodiment, a mapping of a user's mouth is stored in memory such that a specific position within the user's mouth has a specific angle associated therewith. For example, a mold of a user's mouth may be uploaded or downloaded to oral hygiene device 100 or user device 150, such that each position within the user's mouth has an already determined angle. In one embodiment, the mold may be created after a first use of oral hygiene device 100 such that the various angles and positions of a user's mouth are stored in real-time. This may be particularly useful for a user, such as a child, whose mouth may change over time, and thus can readily adapt to any changes that may occur (e.g., lost teeth, palate size increase, etc.).

At step 206, an acceleration sensor within oral hygiene device 100 (e.g., accelerometer 114) may determine an orientation of oral hygiene device 100 with respect to gravity. The angle determined at step 206 may be sent to through a low pass filter at step 208 to filter out any erroneous readings. For example, if a user is moving oral hygiene device 100 very quickly, an accurate angle with respect to gravity may not be attainable and thus these readings may be filtered out.

At step 210, the angle of oral hygiene device 100 with respect to gravity is computed. For example, if accelerometer 114 of oral hygiene device 100 is oriented substantially parallel to the direction of gravity then an approximate zero angle is computed. As another example, the angle computed at step 210 may be non-zero. At step 212, a non-zero angle may have its sign determined. For example, based on whether the user is holding oral hygiene device in their left or right hand, or whether the user is holding oral hygiene device closer to, or further from their mouth, or based on any other factor, the sign of the angle computed at step 210 is determined. For example, if the angle with respect to gravity is 10 degrees, a positive sign, or +1 is obtained, whereas if the angle with respect to gravity is −10 degrees, a negative sign, or −1 is obtained.

After the sign of the computed angle is obtained, it is multiplied with the corresponding offset at step 214. For example if the offset is 30 degrees and the obtained sign is −1, then the multiplicative factor is −30 degrees. These values are then added to the amount of side force obtained at step 202 to determine a position dependent value for the amount of side force applied by oral hygiene device. Thus, the feedback provided at step 222, in one embodiment, differs than that if no offset correction is provided.

FIG. 6 is an illustrative flowchart of process 300 in accordance with various embodiments. In one exemplary embodiment, oral hygiene device 100 is unbalanced. For example, an amount of force due to gravity may be affected by the force applied to attachment assembly 112 based on a variety of factors including, but not limited to, a portion of the user's mouth that attachment assembly 112 is in contact with, a load on attachment assembly 112, a type of attachment assembly 112, or any other factor, or any combination thereof. Due to these factors, an amount of compensation due to gravity is needed to be determined. In one embodiment, the amount of gravitational force is measured with a 3-D MEMS accelerometer.

Process 300 begins at step 302 where an amount of side force is measured by one or more of sensors 104a and 104b of oral hygiene device 100. For example, if the user applies attachment assembly 112 of oral hygiene device 100 to surface 50 (e.g., FIG. 3B) at an angle, the amount of side force may be non-zero and thus proper application or oral hygiene device 100 may not be occurring. In one embodiment, however, oral hygiene device 100 is not balanced and there is an additional force felt by attachment assembly 112 that is not due to an applied force from the user. For example, if attachment assembly 112 has toothpaste, saliva, and/or water on it, the force on attachment assembly 112 will be different than if there was nothing on it. This extra force is accounted for by applying accelerometer 114 to oral hygiene device 100 at step 304 to determine an amount of force felt by oral hygiene device due to gravity.

Figure 6A:
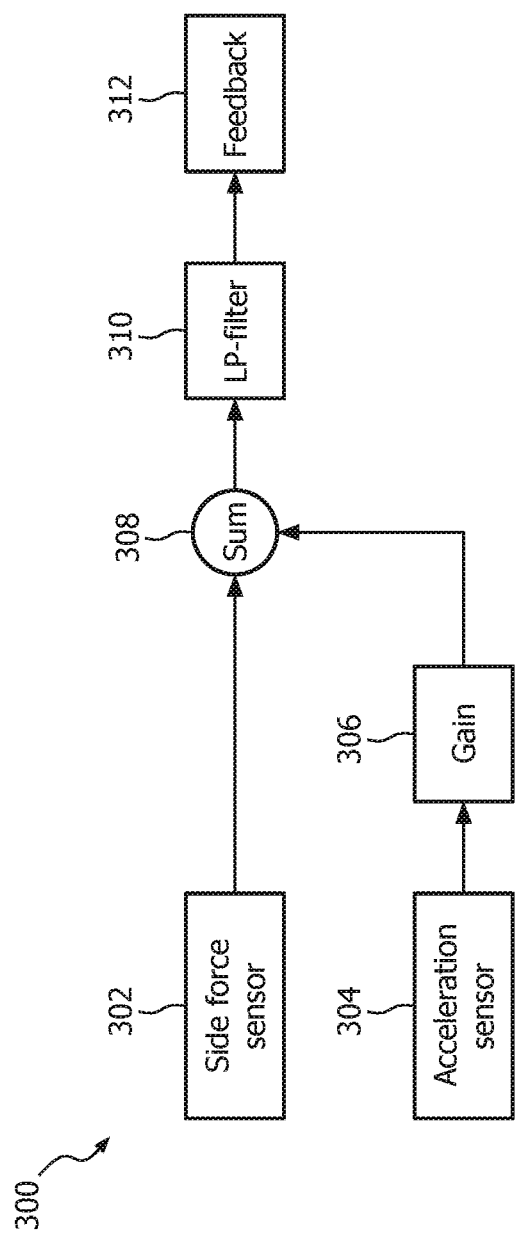
FIG. 6A is an illustrative flowchart of a process 300 in accordance with various embodiments.
Figure 6C:
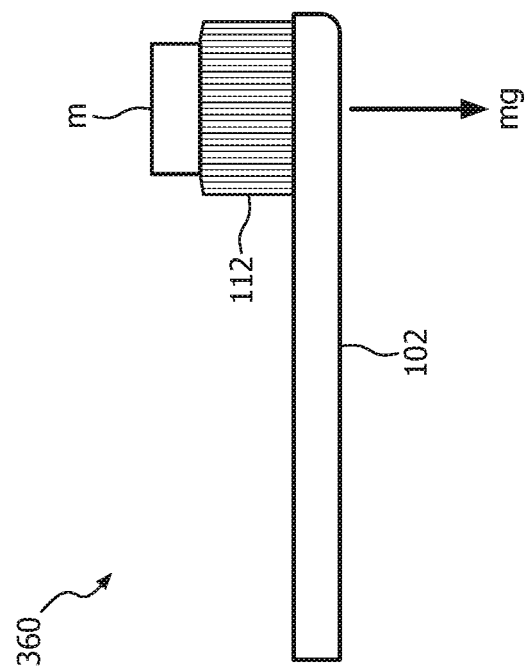
FIGS. 6B and 6C are illustrative diagrams of attachment assembly 112 having no external mass applied thereto, and mass m being applied to attachment assembly 112, respectively, in accordance with various embodiments.
Figure 6B:
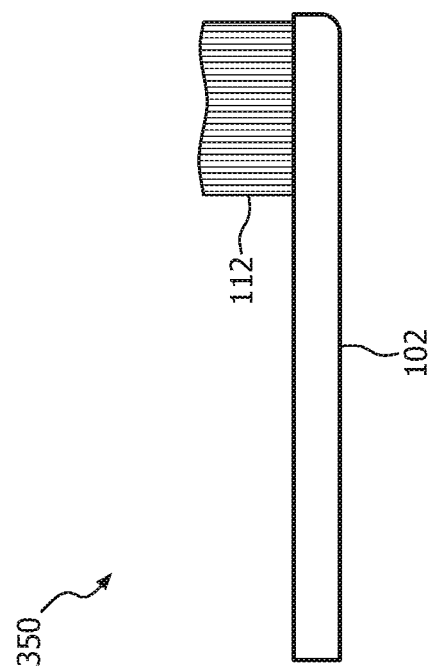

FIGS. 6B and 6C are illustrative diagrams of attachment assembly 112 having no external mass applied thereto, as well as an additional mass m being applied to attachment assembly 112 in accordance with various embodiments. A system 350 is an exemplary embodiment where attachment assembly 112 has no mass applied to it. For example, prior to being used within a user's mouth, no toothbrush and/or water or saliva may contact attachment assembly 112 of oral hygiene device 100. A system 360, however, is another exemplary embodiment where mass m is applied to attachment assembly 112 of oral hygiene device 100 such that a gravitational force mg is felt by attachment assembly 112. In one embodiment, accelerometer 114 of oral hygiene device 100 is able to determine that mass m has been applied to attachment assembly 112, as well as determine a magnitude and/or direction of the gravitational force mg.

Returning to process 300 of FIG. 6A, at step 304 an acceleration sensor measures a gravitational force affecting oral hygiene device 100. For example, as shown in FIG. 6C, mass m exerts force mg on attachment assembly 112 of oral hygiene device 100. This force is measured at step 304 and the gain needed to compensate for force mg is accounted for at step 306. At step 308, the gain and gravitational offset is added to the measured side force obtained from step 302. After combined, the sum is sent through a low pass filter at step 310 to remove any affect that would not be attributed to gravity. For example, gravitational force on attachment assembly 112 are typically low in frequency, so anything higher than the cutoff value of the low pass filter of step 310 is removed. Process 300 then proceeds to step 312 where feedback is provided to the user, where the feedback accounts for the gravitational effects on oral hygiene device 100.

In one exemplary embodiment, processes 200 and 300 may be performed together (e.g., in parallel or sequentially) such that the feedback provided to the user at steps 222 and/or 312 include position offset correction and gravitational compensation. For example, the side force measurement of steps 202 and 302 may be substantially the same except for the fact that the former may be used for position offset and the latter may be used for gravitational compensation. As another example, the acceleration sensor measurement of steps 206 and 304 may be substantially similar except for the fact that the former may be used in combination with a position estimation for a position offset determination, and the latter may be used for determining an applied load to attachment assembly 112.

FIG. 7 is an illustrative flowchart of a process 400 in accordance with various embodiments. In one exemplary embodiment, process 400 describes a way for feedback provided to the user to be adjusted by a sensitivity factor to account for any inexperience or unfamiliarity that the user has for operating oral hygiene device 100. Process 400 begins at step 402. At step 402, one or more sensors 104a, 104b on oral hygiene device 100 measure an amount of side force applied by attachment assembly 112. The measurement is then sent through a low pass filter at step 404 to remove high frequency signals. Steps 402 and 404 are, in one embodiment, substantially similar to steps 202 and 204 of process 200, and the previous description may apply.

A first sensitivity factor is set for providing feedback to the user and maintained for a first amount of time. For example, a first sensitivity factor of 0.1 may be applied such that the feedback provided to the user is less sensitive to fast or non-uniform movements. Gradually, the sensitivity factor is increased such that the feedback is more sensitive to the user's motion until the sensitivity factor is 1. The quickness with which the sensitivity factor increases from the first sensitivity factor to the final sensitivity factor is defined as the learning curve.

At step 406, the time of use is determined. For example, the time measured from the first use of oral hygiene device 100 to the next use, or the number of times that oral hygiene device is operated, or the number of times that oral hygiene device is turned on, may define the time of use. The time of use determined at step 406 may be correlated with the learning curve at step 408 to determine how sensitive the feedback should be, and this factor is incorporated into the measured side force at step 410. At step 410, the sensitivity factor from the learning curve is multiplied by the side force measurement, and then the appropriate feedback is provided to the user at step 412. In one embodiment, each user operating oral hygiene device 100 has a different time of use and learning curve, such that each is made user specific/programmable.

Figure 8:
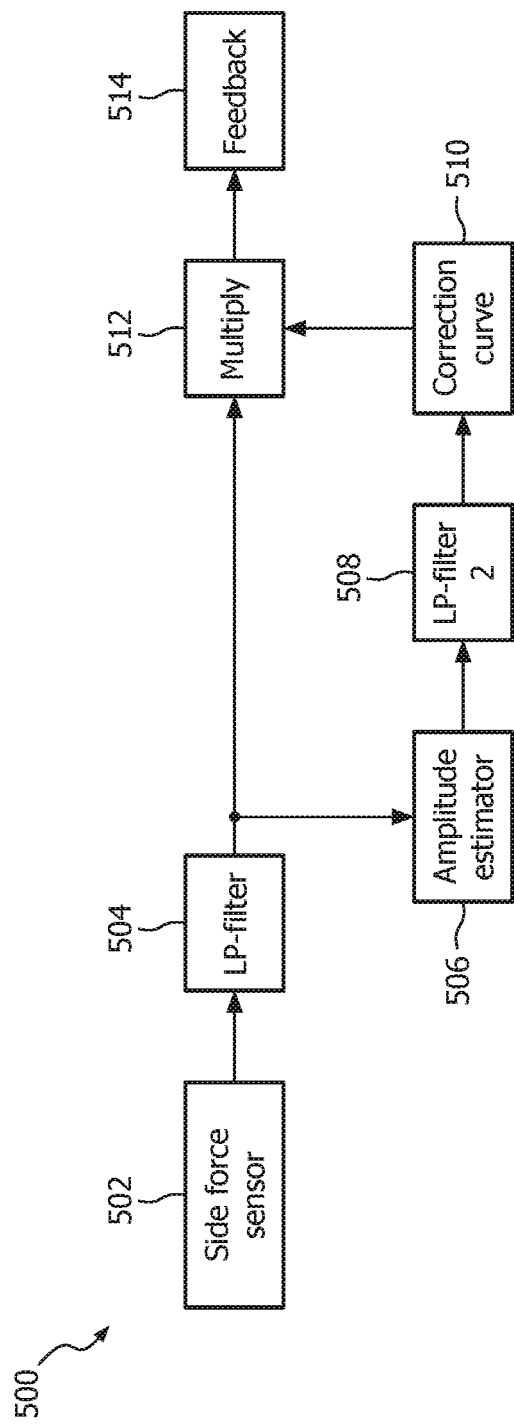
FIG. 8 is an illustrative flowchart of a process 500 in accordance with various embodiments.

FIG. 8 is an illustrative flowchart of a process 500 in accordance with various embodiments. Process 500, in one embodiment, begins at step 502 where a side force measurement occurs and then the measurement passes through a low pass filter at step 504. Steps 502 and 504, in one embodiment, are substantially similar to steps 402 and 404 of process 400, and the previous description may apply.

Process 500, in one embodiment, then proceeds to step 506, where an amplitude of motion of oral hygiene device 100 is estimated. In one embodiment, a root mean square ("RMS") value of the amplitude of motion of oral hygiene device is used. For example, a certain amount of time may be used to estimate the amplitude of oral hygiene device 100 where the RMS value is determined by the summation of the square of each amplitude value at each sampling point, divided by the total number of samples taken, whose square root is then taken.

At step 508, a second low pass filter is applied to the estimated amplitude to filter out small variations in the estimated amplitude. The second low pass filter, in one embodiment, has a larger time constant than the first low pass filter used at step 504. After application of the second low pass filter at step 508, a correction curve is applied to the estimated amplitude at step 510. The correction curve thus adaptively accounts for the brushing amplitude of the user, and accordingly applies a correct sensitivity factor for presenting feedback to the user. In one embodiment, the correction curve uses an inverse of the RMS value obtained at step 506 and multiplies this value with a fixed number to define the sensitivity factor for the user. At step 512, the correction curve factor obtained at step 510 is multiplied by the measured amount of side force, and appropriate feedback is provided to the user at step 514. In one embodiment, steps 512 and 514 are substantially similar to steps 410 and 412 of process 400.

Persons of ordinary skill in the art will recognize that any number of steps from processes 200, 300, 400, and/or 500 may occur on either of oral hygiene device 100 and user device 150. For example, sensor measurements, such as steps 202, 206, and/or 216 of process 200 may occur on oral hygiene device 100, whereas steps 204-222 may occur on user device 150. As another example, steps 402, 404, and 406 of process 400 may occur on oral hygiene device 100, while steps 408-412 may occur on user device 150. These, however, are merely exemplary, and any combination of steps may be performed across either oral hygiene device 100 and/or user device 150.

Figure 9:
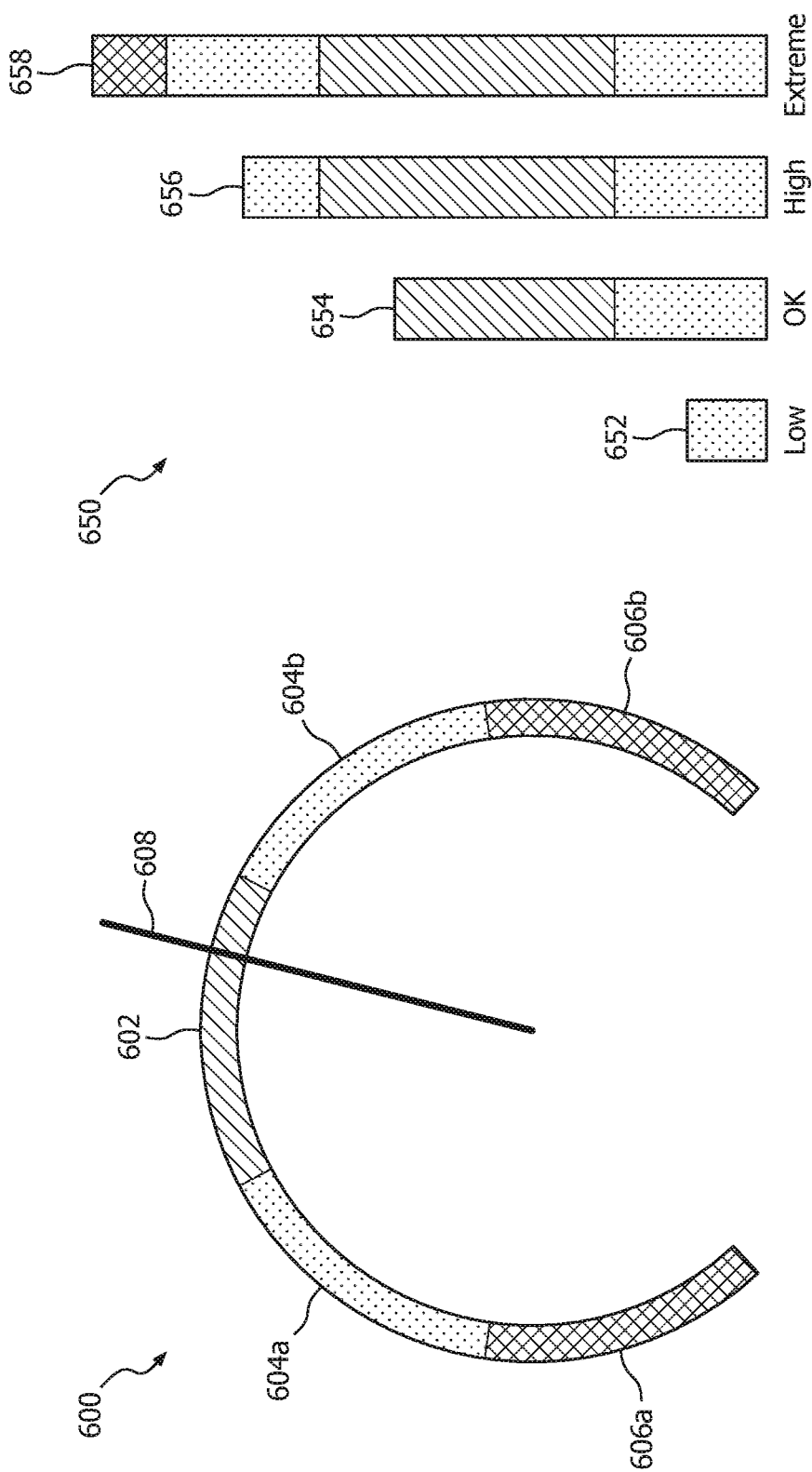
FIG. 9 is an illustrative diagram of an angle indicator 600 in accordance with various embodiments.

FIG. 9 is an illustrative diagram of angle indicator 600 in accordance with various embodiments. Angle indicator 600, in the illustrative exemplary embodiment, displays a substantially circular angle indicator having a first angle region 602, a second angle region 604a, 604b, and a third angle region 606a, 606b. In one embodiment, first angle region 602 corresponds to a correct, or substantially correct angle of operation of oral hygiene device 100. For example, when an amount of side force measured by sensors 104a, 104b of oral hygiene device 100 is determined to be substantially zero, the angle of attachment assembly 112 of oral hygiene device 100 is substantially perpendicular. Thus, first angle region 602 may include angles ranging from −5 degrees to +5 degrees. A user may be able to see the angle that attachment assembly 112 of oral hygiene device 100 is currently being used at via an indicator line 608. When indicator line 608 lies within first angle region 602, the user knows that the angle that attachment assembly 112 is interfacing with surface 50 (e.g., their teeth) is substantially perpendicular to surface 50, and therefore correct. This means that proper operation and application of oral hygiene device 100 is occurring.

If, however, indicator 608 falls within second angle region 604a or 604b, then the angle that attachment assembly 112 is interfacing with surface 50 is greater the angle corresponding to first angle region 602. For example, if first angle region 602 includes angles from −5 degrees to +5 degrees, second region 604a or 604b may include angles from −15 to −5 degrees and +15 to +5 degrees, respectively. In one embodiment, second region 604a corresponds to an angle that is too far to the left, whereas region 604b corresponds to an angle that is too far to the right. For example, when indicator 608 is within region 604a, the angle of attachment assembly 112 with respect to surface 50 may be between −15 and −5 degrees from the normal of surface 50. Persons of ordinary skill in the art will recognize that the aforementioned angles for second angle regions 604a, 604b are merely exemplary, and any range of angles may be used within second angle regions 604a, 604b. Furthermore, these angles may be set by the user, by an oral hygiene professional, or by any other individual with access to oral hygiene device 100 and/or user device 150 (e.g., a parent or guardian of a user of oral hygiene device 100).

First angle region 602, in one embodiment, is a first color, such as green, while second angle regions 604a, 604b are a second color, such as yellow. The color differentiation between first and second angle regions 602 and 604a, 604b allows a user to visually observe when operation of oral hygiene device 100 moves from being within a satisfactory angle range to being in an unsatisfactory angle range, or vice versa. For example, if indicator 608 is in first angle region 602, the user will know that their brushing angle is good and they are using oral hygiene device 100 at a suitable angle to obtain maximum brushing results. However, if indicator 608 move from first region 602 to second region 604a, the user will know that their brushing angle has increased beyond the range for obtaining maximum brushing results, and therefore the user is not brushing at a suitable angle to obtain effective oral hygiene care.

Third angle regions 606a, 606b correspond to angles exceeding the ranges defined by second angle regions 604a, 604b. For example, if second angle region 604a includes angles from −15 degrees to −5 degrees, third angle region 606a may include angles greater than −15 degrees (e.g., −20, −30, −50 degrees, etc.). Similarly, if second angle region 604b includes angles from +15 degrees to +5 degrees, then third angle region 606b may include angles greater than +15 degrees (e.g., +20, +30, +50 degrees, etc.). In one embodiment, regions 606a, 606b include any angle greater than those encompassed by second angle regions 604a, 604b, whereas in another embodiment, third angle regions 606a, 606b are finite and include a range of angles (e.g., −30 degrees to −15 degrees, +30 degrees to +15 degrees).

Third angle regions 606a, 606b, in one embodiment, are a third color, such as red. The color differentiation between third angle regions 606a, 606b, and second angle regions 604a, 604b, allow a user to recognize when the angle of oral hygiene device 100 has gone past the unsatisfactory brushing angle region and has entered into the ineffective or dangerous area. For example, if indicator 608 falls with third region 606a, a user may be brushing at an angle that is too great for any effective oral hygiene care to occur. The different colors between regions allows the user to clearly see when their brushing angle, or angle of use, of oral hygiene device 100 has entered into a good (e.g., first angle region 602), satisfactory (e.g., second angle regions 604a, 604b), or bad (e.g., third angle regions 606a, 606b) area.

In one embodiment, as a user operating oral hygiene device 100 increases their angle of operation of oral hygiene device 100 too far to the left, indicator 608 moves more and more counter clockwise, such as into regions 604a, 606a. Similarly, if the angle of operation of oral hygiene device 100 increases too much to the right, indicator 608 moves more and more clockwise, such as into regions 604b, 606b. For example, a user whose brushing angle increases from 0 degrees to −10 degrees will see indicator 608 move from first angle region 602 to second angle region 604a. As another example, if a user's brushing angle increases from +10 degrees to +30 degrees, indicator 608 will move from second angle region 604b to third angle region 606b.

In one embodiment, the direction of movement of indicator 608 will change depending on the hand used to operate oral hygiene device 100. For example, if the user operates oral hygiene device 100 with their right hand, as brushing angles increase, indicator 608 may move to the right, whereas as brushing angles decrease, indicator 608 may move to the left. Conversely, if the user operates oral hygiene device 100 with their left hand, increase in brushing angle may cause indicator 608 to move to the left, and decrease in brushing angle may cause indicator 608 to move to the right.

Persons of ordinary skill in the art will recognize that any color scheme for first, second, and/or third angle regions 602, 604a, 604b, 606a, 606b may be used, and may be set by the user or predefined by oral hygiene device 100 and/or user device 150. Furthermore, any angle range may be used for each region, and the aforementioned are merely exemplary. Still further, any increase in angle may cause indicator 608 to move in any suitable direction so long as a change in angle in one direction has a linear relationship to a direction of motion of indicator 608 and a change in angle in an opposite direction causes indicator 608 to move in the opposite direction (e.g., as angle increases, indicator 608 moves to the right and as angle decreases, indicator 608 moves to the left).

Figure 10:
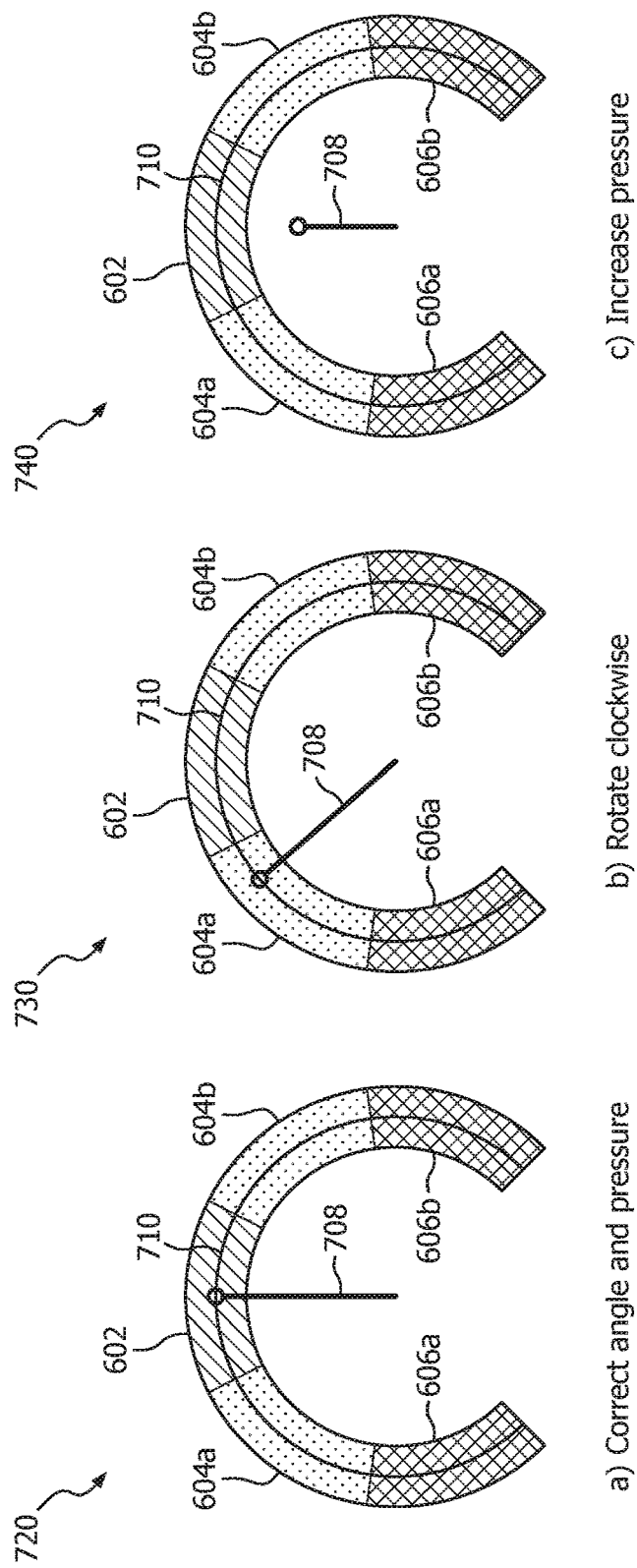
FIG. 10 is an illustrative diagram of a pressure indicator 650 in accordance with various embodiments.
Figure 11:
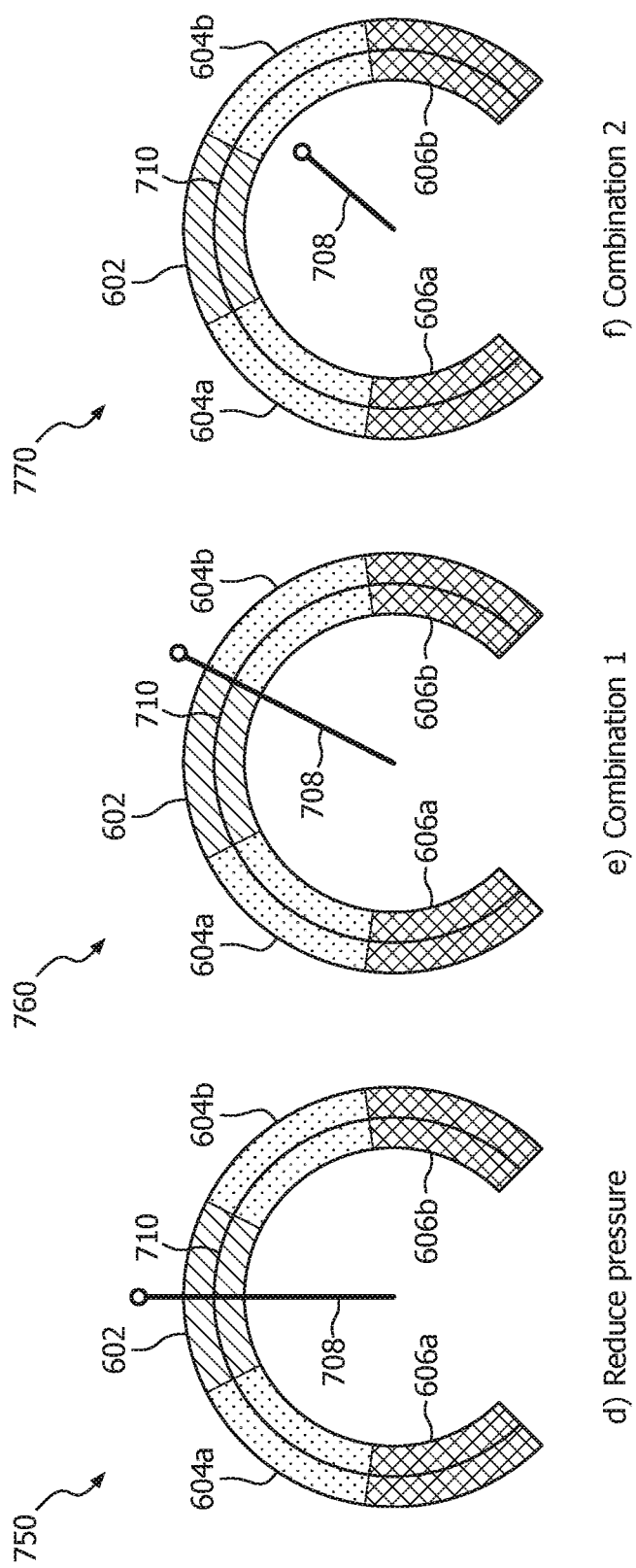
FIGS. 11A-F are illustrative diagrams of combined indicators 720, 730, 740, 750, and 760 in accordance with various embodiments.

FIG. 10 is an illustrative diagram of a pressure indicator 650 in accordance with various embodiments. Pressure indicator 650 corresponds, in one exemplary embodiment, to a pressure indicator that indicates an amount of pressure being applied to surface 50 (e.g., a user's teeth) by attachment assembly 112 of oral hygiene device 100. Pressure indicator 650, in one embodiment, is operable to display to a user operating oral hygiene device 100 an indication of an amount of pressure that they are applying with oral hygiene device 100, and whether that amount of pressure is too low, correct, or too high.

If the amount of pressure applied by the user via oral hygiene device 100 is too low, pressure indicator 650 will display a first pressure bar 652. First pressure bar 652 represents an amount of pressure that is lower than a preset amount of pressure needed for accurate oral hygiene care. If the pressure applied by the user is correct, a second pressure bar 654 will be presented by pressure indicator 650. When pressure indicator 650 displays second pressure bar 654, the user will know that they are applying the correct amount of pressure to surface 50 (e.g., the user's teeth) to provide proper oral hygiene care. If, however, the pressure applied by the user is too great, then one of a third or fourth pressure bar 656, 658 will be presented by pressure indicator 650. For example, if the applied pressure is slightly too high, then pressure indicator will display third pressure bar 656, whereas if the pressure is extremely high, and may damage to one's teeth and/or gums, then pressure indicator 650 will present fourth pressure bar 658.

In one exemplary embodiment, pressure indicator 650 is displayed alongside angle indicator 600 so that the user is aware of both the angle and pressure level of their oral hygiene device. For example, if the user's angle is correct and pressure is good, then indicator 608 will be within first angle region 602, and pressure indicator 650 will display second pressure bar 654.

In another exemplary embodiment, pressure indicator 650 will only be displayed if the angle of operation of oral hygiene device 100 is within a suitable range. For example, if the angle of attachment assembly 112 of oral hygiene device 100 is substantially perpendicular to surface 50 (e.g., a user's teeth), then pressure indicator 650 will display a pressure level of attachment assembly 112. In this particular scenario, if the angle of attachment assembly 112 no longer is substantially perpendicular to surface 50, pressure indicator 650 will no long display a pressure level.

In yet another exemplary embodiment, pressure indicator 650 is displayed only after angle indicator 600 displays indicator 608 within first angle region 602. For example, a user may maneuver oral hygiene device 100 until the angle of attachment assembly 112 with respect to surface 50 falls within the bounds of first angle region 602. After this occurs, pressure indicator 650 will appear to the user so that the user is capable of knowing if they are applying a correct amount of pressure via oral hygiene device 100.

FIGS. 11A-F are illustrative diagrams of combined indicators 720, 730, 740, 750, and 760 in accordance with various embodiments. Each of combined indicators 720, 730, 740, 750, and 760 display a combined angle and pressure indicator such that a user operating oral hygiene device 100 is capable of knowing if they are applying a correct amount of pressure at a correct angle at a substantially same time. Each combined indicator 720, 730, 740, 750, and 760 includes first angle region 602, second angle regions 604a, 604b, and third angle regions 606a, 606b, as well as a nominal pressure line 710. Nominal pressure line 710 indicates a correct pressure level for oral hygiene device 100 throughout each angle region.

Combined indicator 720, in one embodiment, displays an indicator 708 having a correct angle and a correct pressure level. This is seen by indicator 708 being within first angle region 602 and being at nominal pressure line 710. If a user is applying too much pressure in a counter clockwise direction (e.g., too far left), but still is applying a correct amount of pressure, combined indicator 730 is displayed. In combined indicator 730, indicator 708 is at nominal pressure line 710, indicating a correct amount of pressure, however indicator 708 is also within second angle region 604a. This means, for example, that the user operating oral hygiene device 100 has attachment assembly 112 at too great of a counter clock-wise angle with respect to surface 50, and therefore instructions to rotate oral hygiene device 100 clockwise are provided within combined indicator 730.

Combined indicator 740, in one embodiment, displays indicator 708 having a correct angle, but too low a pressure. Indicator 708 is below nominal pressure line 710, indicating that pressure is lower than a correct pressure level for correct oral hygiene care. However, because indicator 708 is still positioned such that it lies within the range of angles encompassed by first angle region 602, no change in angle of oral hygiene device 100 is needed. Combined indicator 750 is substantially similar to combined indicator 740, with the exception that the former indicates that oral hygiene device 100 is being applied with too much pressure. For example, indicator 708 exceeds nominal pressure level 710, and therefore means that the amount of pressure being applied is greater than needed for adequate oral hygiene car.

Combined indicator 760, in one embodiment, displays indicator 708 having a pressure level exceeding nominal pressure line 710, and being at an angle slightly greater than first angle region 602. For example, the user operating oral hygiene device 100 may be applying too much pressure, and therefore indicator 708 extends past nominal pressure line 710. Furthermore, attachment assembly 112 of oral hygiene device 100 may be applied at +7 degrees, which may be slightly outside the range of first angle region 602, which includes angles between −5 and +5 degrees. In this particular scenario, instructions to decrease the amount of pressure and rotate oral hygiene device counter clock-wise may be provided to the user such that the user may obtain proper pressure and angle levels for correct oral hygiene care (e.g., see combined indicator 720).

Combined indicator 770, in one embodiment, displays indicator 708 having a pressure level lower than nominal pressure line 710, and being at an angle slightly greater than first angle region 602. For example the user operating oral hygiene device 100 may be applying too little pressure, and therefore indicator 708 fails to reach nominal pressure line 710. Furthermore, as described above, attachment assembly 112 of oral hygiene device may be slightly outside the range of first angle region 602, such within second angle region 604b. In this particular scenario, instructions to increase the amount of pressure applied by oral hygiene device rotate oral hygiene device counter clock-wise may be provided to the user visually by combined interface 770.

In one exemplary embodiment, audio and/or visual indicators may also be provided to the user in addition to, or instead of, combined indicators 720-770. For example, if indicator 760 is presented, audio instructions telling the user to decrease the amount of applied pressure and rotate the angle of oral hygiene device 100 may be outputted by one or oral hygiene device 100 and/or user device 150. As another example, written instruction informing the user to decrease pressure and rotate oral hygiene device 100 may be displayed with combined indicator 760.

In one exemplary embodiment, specific instructions are provided to the user by combined indicators 720-770. For example, if the angle of attachment assembly 112 of oral hygiene device 100 is +15 degrees with respect to surface 50, instructions to rotate oral hygiene device 100 by at least 10 degrees counter clock-wise may be provided. As another example, if the pressure applied by oral hygiene device 100 is too great, instructions may be provided to decrease the amount of pressure applied by oral hygiene device 100.

Persons of ordinary skill in the art will recognize that any of angle indicator 600, pressure indicator 650, and combined indicators 720-770 may be displayed on any display screen operable to present a user interface. For example, display 134 of oral hygiene device 100 or user device 150 may present angle indicator 600, pressure indicator 650, and/or combined indicators 720-770 to a user operating oral hygiene device 100.

Figure 12:
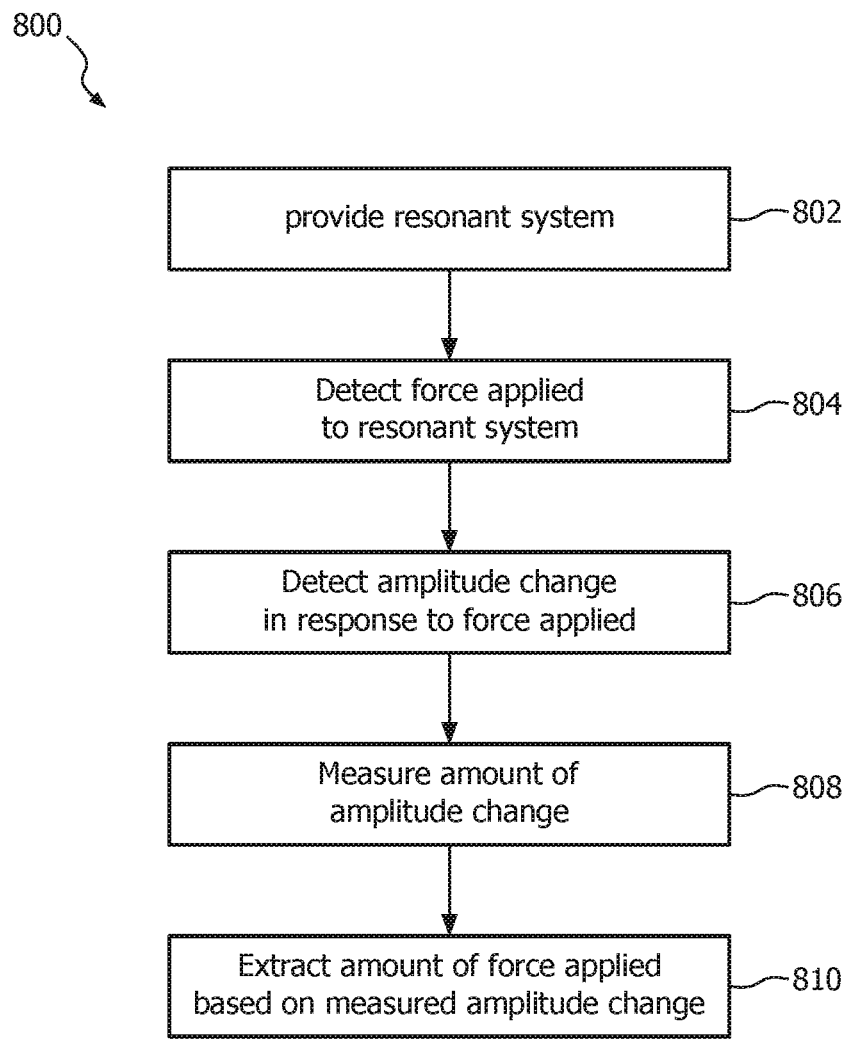
FIG. 12 is an illustrative flowchart of a process 800 in accordance with various embodiments.

FIG. 12 is an illustrative flowchart of process 800 in accordance with various embodiments. In the illustrative exemplary embodiment, a process for indirectly measuring an amount of force applied to attachment assembly 112 of oral hygiene device 100 is provided. For example, an amount of side force applied to attachment assembly 112 (e.g., FIGS. 3A and 3B) is capable of determined indirectly from the natural dynamic behavior of oral hygiene device 100 due to various load conditions.

Process 800 begins at a step 802. At step 802, a resonant system, such as oral hygiene device 100, is provided. Oral hygiene device 100, in one embodiment, operates at a resonant frequency. In particular, drive train assembly 124 operates at a driving frequency from power system 126, which causes attachment assembly 112 to vibrate at a certain amplitude. The vibrations of oral hygiene device 100 occur at the natural resonant frequency of oral hygiene device 100 due to no additional forces or mass being applied to any portion of oral hygiene device 100.

Process 800 then proceeds to a step 804. At step 804, an amount of force applied to the resonant system is detected. In one embodiment, as a user places attachment assembly 112 inside their mouth, interactions with the user's teeth, gums, and/or saliva, acts as an additional force applied to oral hygiene device 100, changing the balance and load conditions of oral hygiene device 100. In one embodiment, applying toothpaste or other masses to attachment assembly 112 prior to placing attachment assembly 112 inside the user's mouth are also capable of modifying the load conditions of oral hygiene device 100. However, in this particular scenario, oral hygiene device 100 is capable of storing the load conditions associated with application of certain masses so that they can be accounted for. For example, the amount of toothpaste typically applied to attachment assembly 112 of oral hygiene device 100 is fairly consistent, and therefore, the amount of force applied to attachment assembly 112 by the toothpaste may be an offset used in calculating the amount of normal and side force felt by attachment assembly 112 when in use.

Process 800 then proceeds to a step 806. At step 806, a change in the amplitude of attachment assembly 112 of oral hygiene device 100 is detected based on the amount of force applied in step 804. Due to the fact that oral hygiene device 100 is a substantially resonant system, modification to the amount of load of attachment assembly 112 will modify the natural behavior of oral hygiene device 100. The amplitude of attachment assembly 112 will change as well as a phase of vibration relative to the driving frequency will change. In a resonant system, amplitude and phase characteristics vary greatly around the resonant frequency of the system. Therefore, small changes in the natural frequency of oral hygiene device 100 result in changes to amplitude and phase characteristics of the driving frequency of oral hygiene device 100.

At step 808, the amount of amplitude change of attachment assembly 112 of oral hygiene device 100 is measured. In one embodiment, phase changes or changes in characteristics of the phase of oral hygiene device 100 are also measured. For example, sensors 104a and 104b of oral hygiene device 100 may measure a change in motion of second end 102b of longitudinal shaft 102 based on the applied force to attachment assembly 112 at first end 102a of longitudinal shaft 102.

At step 810, the measured amount of amplitude change of attachment assembly 112 is used to determine how much force has been applied to attachment assembly 112 of oral hygiene device 100. In one embodiment, a look-up table stored in memory 154 is operable to relate amount of amplitude change to amount of force applied. However, in another embodiment, the relationship of applied force and amplitude change may be calculated by processors 132. Persons of ordinary skill in the art will recognize that any suitable technique may be used to determine the amount of force applied to attachment assembly 112 of oral hygiene device 100 based on the measured amplitude and/or phase characteristic changes, and the aforementioned is merely exemplary. For example, synchronization techniques may be used to extract the amount of applied force based on the measured amplitude. Persons of ordinary skill in the art will further recognize that the amount of force extracted may be in any direction, and therefore the amount of normal force and/or side force are extractable from the measured changes to the amplitude and/or phase changes, as these may also be measured across more than one direction.

Figure 13:
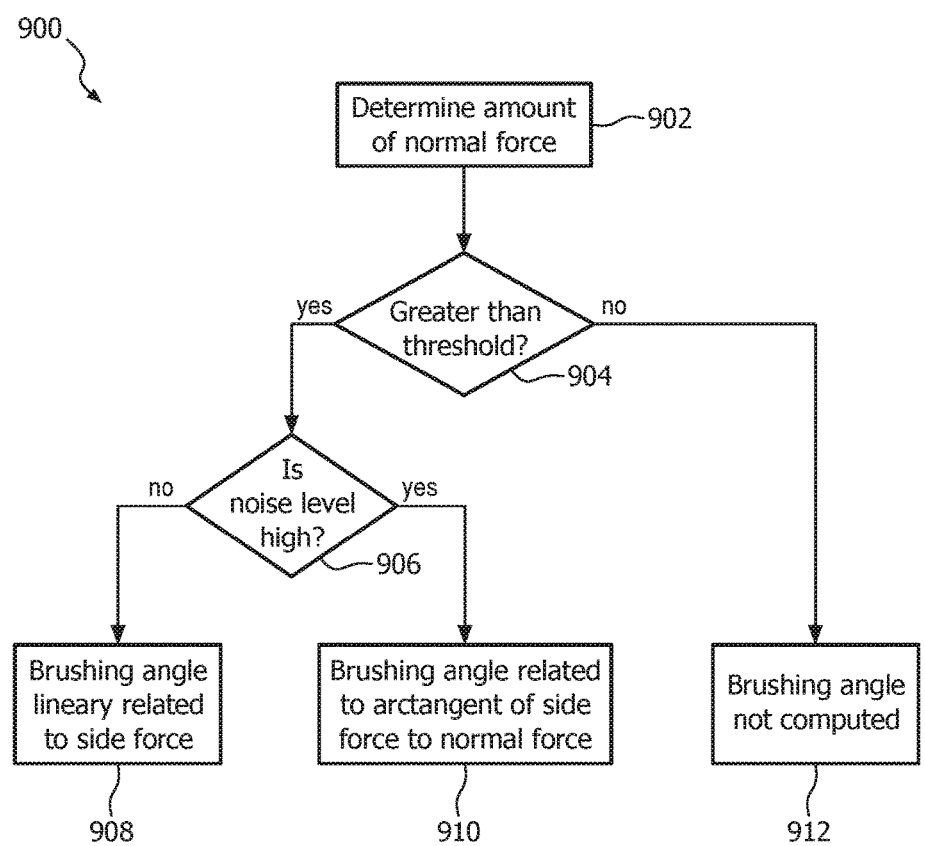
FIG. 13 is an illustrative flowchart of a process 900 in accordance with various embodiments.

FIG. 13 is an illustrative flowchart of process 900 in accordance with various embodiments. Process 900 begins at step 902. At step 902, an amount of normal force applied by attachment assembly 112 of oral hygiene device 100 is determined. Persons of ordinary skill in the art will recognize that various techniques, as illustrated above, may be used to determine the amount of normal force applied by attachment assembly 112. As one illustrative example, sensors 104a and/or 104b are operable to detect an amount of position change of second end 102b of longitudinal shaft 102 with respect to an axis (e.g., y-axis) defining the direction of the normal force relative to a surface, such as surface 50 (e.g., a user's teeth).

At step 904, a determination is made as to whether or not the determined amount of normal force of step 902 is greater than or less than a predefined threshold. For example, if the normal force is greater than or equal to 0.5 N, then the amount of side force will be determined. This may aid in eliminating any extraneous calculations for the side force for scenarios where the applied force is not related to a brushing motion, for example. Persons of ordinary skill in the art will recognize that any threshold value may be used, and the aforementioned is merely exemplary.

If, at step 904, it is determined that the amount of normal force determined at step 902 is less than the threshold, then process 900 proceeds to step 912, where the brushing angle is not computed. In this particular scenario, the force applied to attachment assembly 112 may be erroneous or not related to a brushing action. For example, a user may have just placed toothpaste on attachment assembly 112, or a user may have accidently touched attachment assembly 112 with a non-brushing surface (e.g., counter top, faucet, etc.).

If, at step 904, it is determined that the amount of normal force applied to attachment assembly 112 is greater than the threshold, then process 900 proceeds to step 906. At step 906, another determination is made as to whether the noise level of oral hygiene device is high. In one embodiment, the angle indicator is noisy for low side force levels, and therefore process 900 would proceed to step 910.

At step 910, the brushing angle is determined based on the geometrical relationship between the normal force and the side force. For example, the arctangent of the side force to the normal force yields the angle that attachment assembly 112 interacts with surface 50. If, however, the noise level is not very high, then process 900 proceeds to step 908 where the relationship between the normal force and the side force is substantially linear. For example, if the noise level is low, the angle of attachment assembly 112 with surface 50 may equal the side force. Persons of ordinary skill in the art will recognize that any noise value and any threshold value may be used.

Figure 14:
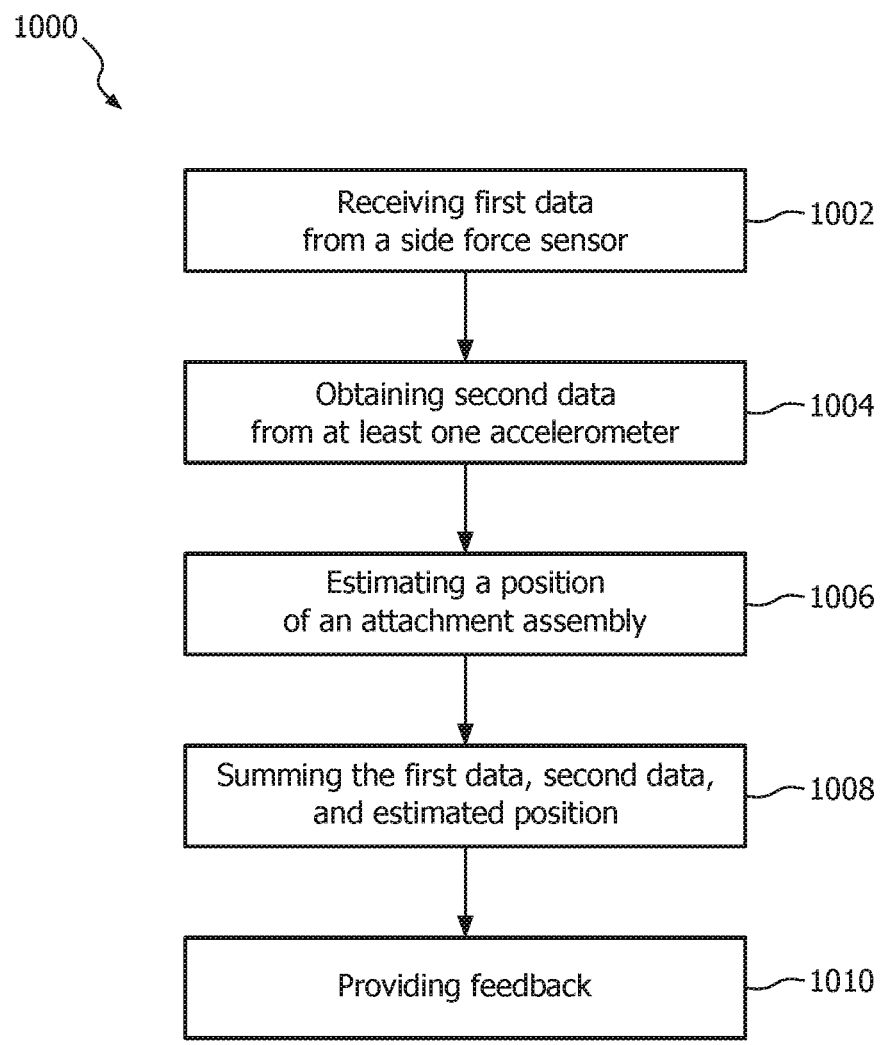
FIG. 14 is an illustrative flowchart of a process 1000 in accordance with various embodiments.

FIG. 14 is an illustrative flowchart of process 1000 in accordance with various embodiments. Process 1000 begins at step 1002. At step 1002, first data is received from a side force sensor located within a handle portion of oral hygiene device 100. For example, sensor 104a, 104b may send data to one or more processors 132 of oral hygiene device 100 and/or user device 150 regarding a position of second end 102b of longitudinal shaft 102 of oral hygiene device 100. The data captured by sensor 104a, 104b, in one embodiment, relates to an amount of side force applied to attachment assembly 112 of oral hygiene device 100.

At step 1004, second data is obtained from accelerometer(s) 114 within handle portion 110 of oral hygiene device 100. The second data, in one embodiment, relates to an amount of force due to gravity felt by oral hygiene device. For example, the amount of force due to gravity may relate to a relative angle of oral hygiene device 100 while in use. As another example, data from accelerometer(s) 114 may correspond to velocity and/or acceleration of oral hygiene device 100 as it is operated by the user.

At step 1006, a position of attachment assembly 112 within the user's mouth is estimated. In one embodiment, oral hygiene device 100 may use data obtained by accelerometer(s) 114 to estimate where in the user's mouth. For example, as seen in FIGS. 5B and 5C, different teeth may be oriented at different angles. Therefore, even if accelerometer(s) 114 detect that oral hygiene device 100 is at an angle, it may not mean that too much side force is being applied, as that particular tooth may be at a different angle. In one embodiment, a look-up table may be used to associate various angles detected by accelerometer(s) 114 with various positions within a user's mouth, such that when a particular angle is detected, oral hygiene device 100 and/or user device 150 is capable of estimating where attachment assembly 112 is within the user's mouth by determining which tooth the user is brushing.

At step 1008, the first data, second data, and estimated position are summed to determine an overall angle and an amount of overall force of attachment assembly 112 of oral hygiene device 100 as it is being applied to the user's teeth. In one embodiment, the estimated brush position and sign of the angle from the accelerometer(s) 114 may corresponds to an offset that is needed to be applied to the first data received from sensors 104a, 104b.

At step 1010, feedback is provided to the user operating oral hygiene device 100 based on the determined overall angle and amount of overall force. For example, a combined interface, such as combined interfaces 720-770, may display a user interface to the user operating oral hygiene device 100 informing the user whether or not their brushing angle is satisfactory and/or whether or not they are applying a correct amount of pressure for correct oral hygiene care.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An oral hygiene device, comprising:
a longitudinal shaft defining a longitudinal axis;
an attachment assembly located at a first end of the longitudinal shaft, the attachment assembly for contacting a contact surface in a user's mouth;
a handle portion comprising:
a portion of the longitudinal shaft comprising a second end of the longitudinal shaft;
a force sensor operable to detect an amount of side force applied to the attachment assembly, the side force comprising a force applied by the contact surface in a direction perpendicular to both the longitudinal axis and the normal of the contact surface, the force sensor comprising a suspension system having at least one elastic spring element and a predefined stiffness for motion in a first direction and a second direction, wherein the first and second direction are both perpendicular to the longitudinal axis of the longitudinal shaft;
at least one accelerometer operable to measure an amount of gravitational force applied to the attachment assembly; and
at least one processor operable to determine an angle that the attachment assembly is applied at based on the detected amount of side force.

2. The oral hygiene device of claim 1, wherein the at least one processor is further operable to:
modify the determined angle based on the amount of gravitational force applied to the attachment assembly measured by the at least one accelerometer.

3. The oral hygiene device of claim 1, further comprising:
communications circuitry operable to send the determined angle to a display screen presenting a user interface that is viewable to a user operating the oral hygiene device.

4. The oral hygiene device of claim 1, wherein:
the attachment assembly comprises a brush head assembly; and
the brush head assembly comprises a plurality of bristles extending away from a bristle member located at the first end of the longitudinal shaft.

5. The oral hygiene device of claim 1, wherein:
the force applied to the attachment assembly comprises a force applied in a first direction and a force applied in a second direction;
the amount of force applied to the attachment assembly in the first direction corresponds to a normal force from interaction between the attachment assembly and the contact surface of a user's mouth, the normal force comprising a force applied by the contact surface in a direction parallel to the normal of the contact surface; and
the amount of force applied to the attachment assembly in the second direction corresponds to the side force from interaction between the attachment assembly and the contact surface of the contact surface of the user's mouth.

6. The oral hygiene device of claim 1,
further comprising a normal force sensor
operable to measure an amount of normal force applied to the attachment assembly, the normal force comprising a force applied by the contact surface in a direction parallel to the normal of the contact surface.

7. An oral hygiene device comprising:
a longitudinal shaft defining a longitudinal axis;
an attachment assembly located at a first end of the longitudinal shaft, the attachment assembly for contacting a contact surface in a user's mouth;
a handle portion comprising:
a portion of the longitudinal shaft comprising a second end of the longitudinal shaft;
a first Hall Effect sensor and a second Hall Effect sensor operable to detect an amount of side force applied to the attachment assembly, the side force comprising a force applied by the contact surface in a direction perpendicular to both the longitudinal axis and the normal of the contact surface wherein the first Hall Effect sensor measures changes in a magnetic field within the handle portion in the first direction;
the second Hall Effect sensor measures changes in the magnetic field within the handle portion in the second direction;
at least one accelerometer operable to measure an amount of gravitational force applied to the attachment assembly; and
at least one processor operable to determine an angle that the attachment assembly is applied at based on the detected amount of side force.

8. A method for providing feedback to a user operating an oral hygiene device regarding a quality of an angle of application of the oral hygiene device relative to a contact surface in the user's mouth, the method comprising:
receiving first data from a side force sensor located within a handle portion of the oral hygiene device, the handle portion defining a longitudinal axis, the first data corresponding to an amount of side force applied to an attachment assembly of the oral hygiene device, the side force comprising a force applied by the contact surface in a direction perpendicular to both the longitudinal axis and the normal of the contact surface;
obtaining second data from at least one acceleration sensor of the oral hygiene device, the second data corresponding to an amount of gravitational force associated with the oral hygiene device;
estimating a position of the attachment assembly within a mouth of a user operating the oral hygiene device;
combining the first data, the second data, and the estimated position to determine an overall angle and an amount of overall force of the attachment assembly as it is being applied; and
providing feedback to the user operating the oral hygiene device, wherein the feedback comprises the overall angle and the overall amount of force of the applied attachment assembly.

9. The method of claim 8, wherein receiving further comprises:
applying a low pass filter to the first data prior to combining.

10. The method of claim 8, wherein obtaining further comprises:
applying a low pass filter to the second data prior to summing;
computing an angle of the attachment assembly with respect to gravity; and
extracting a sign of the computed angle to determine a direction that the attachment assembly is applied.

11. The method of claim 8, wherein estimating further comprises:
accessing an offset value for the attachment assembly based on the estimated position within the user's mouth using a look-up table.

12. The method of claim 11, wherein the offset value corresponds to at least one of:
- a depth of the attachment assembly within the user's mouth;
- a surface type of the user's mouth that the attachment assembly interacts with; and
- an orientation of the oral hygiene device operated by the user.

13. The method of claim 8, wherein the provided feedback further comprises:
- the overall angle and the amount of force applied to the attachment assembly, which is displayed on a graphical user interface presented on a display screen; and
- a direction for the user operating the oral hygiene device to move the attachment assembly to at least one of: improve the overall angle and improve the amount of force applied to the attachment assembly.

\* \* \* \* \*